United States Patent
Hu et al.

(10) Patent No.: US 10,562,905 B2
(45) Date of Patent: Feb. 18, 2020

(54) CARBOXY TETRAHYDROPYRAZOLOPYRAZINE COMPOUNDS FOR THE TREATMENT OF INFECTIOUS DISEASES

(71) Applicant: Hoffmann-La Roche Inc., Little Falls, NJ (US)

(72) Inventors: Taishan Hu, Shanghai (CN); Buyu Kou, Shanghai (CN); Haixia Liu, Shanghai (CN); Zhisen Zhang, Shanghai (CN); Zheng Zhou, Shanghai (CN)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 16/247,084

(22) Filed: Jan. 14, 2019

(65) Prior Publication Data

US 2019/0322670 A1 Oct. 24, 2019

Related U.S. Application Data

(63) Continuation of application No. PCT/EP2017/067319, filed on Jul. 11, 2017.

(30) Foreign Application Priority Data

Jul. 14, 2016 (WO) ................. PCT/CN2016/090036
Apr. 13, 2017 (WO) ................. PCT/CN2017/080438

(51) Int. Cl.
    C07D 487/04    (2006.01)
    C07D 487/08    (2006.01)
    C07D 498/08    (2006.01)
    A61P 31/20     (2006.01)

(52) U.S. Cl.
    CPC ............ C07D 487/04 (2013.01); A61P 31/20 (2018.01); C07D 487/08 (2013.01); C07D 498/08 (2013.01)

(58) Field of Classification Search
    CPC ..................... C07D 487/04; C07D 487/08
    See application file for complete search history.

(56) References Cited

U.S. PATENT DOCUMENTS

| | | |
|---|---|---|
| 9,890,167 B2 | 2/2018 | Hu et al. |
| 2018/0334461 A1 | 11/2018 | Hu et al. |
| 2019/0185476 A1 | 6/2019 | Hu et al. |

FOREIGN PATENT DOCUMENTS

| | | |
|---|---|---|
| WO | 2009/085983 A1 | 7/2009 |
| WO | 2013/096744 A1 | 6/2013 |
| WO | 2014/033167 A1 | 3/2014 |
| WO | 2014/033170 A1 | 3/2014 |
| WO | 2014/111871 A1 | 7/2014 |
| WO | 2014/152725 A1 | 9/2014 |
| WO | 2016/109689 A2 | 7/2016 |
| WO | 2016/109689 A3 | 7/2016 |
| WO | 2016/113273 A1 | 7/2016 |
| WO | 2017/198744 A1 | 11/2017 |

OTHER PUBLICATIONS

Barsanti et al., "Structure-Based Drug Design of Novel Potent and Selective Tetrahydropyrazolo[1,5-a]pyrazined as ATR Inhibitors" ACS Medicinal Chemistry Letters 6(1):37-41 ( 2014).
ISR and Written Opinion for PCT/EP2017/067319 (dated Sep. 26, 2017).

*Primary Examiner* — Laura L Stockton
(74) *Attorney, Agent, or Firm* — Genentech, Inc.; Richard G. A. Bone

(57) ABSTRACT

The present invention relates to compounds of the formula (I),

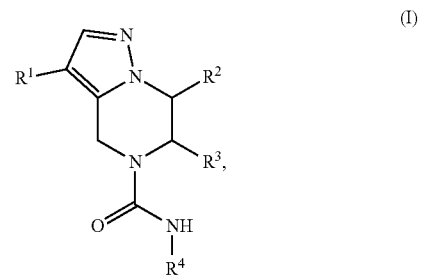

or pharmaceutically acceptable salts, enantiomer or diastereomer thereof, wherein $R^1$ to $R^3$ are as described above. The compounds may be useful for the treatment or prophylaxis of hepatitis B virus infection.

6 Claims, No Drawings

CARBOXY TETRAHYDROPYRAZOLOPYRAZINE COMPOUNDS FOR THE TREATMENT OF INFECTIOUS DISEASES

RELATED APPLICATIONS

This application is a Continuation of International Application No. PCT/EP2017/067319, filed Jul. 11, 2017, claiming priority to Application No. PCT/CN2016/090036, filed Jul. 14, 2016 and Application No. PCT/CN2017/080438, filed Apr. 13, 2017, each of which are incorporated herein by reference in its entirety.

The present invention relates to organic compounds useful for therapy and/or prophylaxis in a mammal, and in particular for treating hepatitis B virus infection, and their pharmaceutical activity, manufacture, pharmaceutical compositions containing them and their potential use as medicaments.

FIELD OF THE INVENTION

The present invention relates to compounds of the formula (I),

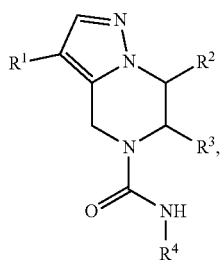

(I)

or pharmaceutically acceptable salts, enantiomer or diastereomer thereof, wherein $R^1$ to $R^4$ are as described below. The compounds of this invention are useful for the treatment or prophylaxis of hepatitis B virus infection.

Hepatitis B virus (HBV) infection is a major public health problem worldwide, roughly 30% of the world's population show serological evidence of current or past infection. Despite the introduction of a safe and effective prophylactic vaccine against the virus in the early 1980s, it is estimated that there are still more than 240 million chronic HBV carriers worldwide, a high percentage of whom will eventually develop liver cirrhosis or hepatocellular carcinoma (HCC) (WHO Hepatitis B. Fact Sheet No 204). In the 2010 Global Burden of Disease study (R Lozano, et al. Lancet, 380 (2012), 2095-2128), HBV infection ranked in the top health priorities in the world, and was the tenth leading cause of death (780,000 deaths per year). Recent studies have shown that progression to liver cirrhosis and HCC in patients with chronic HBV infection is significantly associated with circulating HBV DNA levels. Thus, antiviral therapy against HBV is critical to prevent the progression to cirrhosis or development of HCC.

HBV is a small, enveloped virus that belongs to the Hepadnaviridae family. It contains a partly double-stranded DNA genome with approximately 3200 base pairs. HBV have a strong preference for infecting human hepatocytes. The life cycle begins when HBV attaches to the host cell membrane via its envelope proteins. The precise mechanism of viral entry has not been fully elucidated. The viral relaxed circular DNA (rcDNA) containing nucleocapsids are released into the cytoplasm and transported to the nucleus. In the nucleus, the rcDNA is repaired by both viral and cellular enzymes to form covalently closed circular DNA (cccDNA). There is evidence that each infected cell contains 1-50 cccDNA molecules as unique episomal minichromosomes. Both subgenomic RNA (sgRNA) and pregenomic RNA (pgRNA) are transcribed from the cccDNA using the cellular transcriptional machinery. After nuclear export, the pgRNA is translated into the core protein and the viral polymerase. The sgRNA is translated into the regulatory X protein and the three envelope proteins. Self-assembly of the RNA-containing viral nucleocapsid takes place via complex formation of the pgRNA with the core protein and the polymerase. Inside the nucleocapsid, the pgRNA is reverse transcribed into negative-strand DNA. rcDNA is then generated by plus-strand synthesis from the negative-strand DNA. The nucleocapsids are either re-imported to the nucleus for cccDNA amplification or enveloped and released via the endoplasmic reticulum (ER). The reverse transcriptase lacks proofreading activity; thus, mutations of the viral genome are frequent and result in the coexistence of genetically distinct viral species in infected individuals (quasispecies).

Currently, seven treatments are approved for chronic hepatitis B (CHB), including two formulations of interferon (IFN) (conventional IFN and PEG-IFN) and five nucleos(t)ide analogues (NUCs: lamivudine, adefovir dipivoxil, entecavir, telbivudine, and tenofovir disoproxil). The main difference between immunomodulatory agents and NUCs is that PEG-IFN has the advantage of a finite duration of use, whereas the use of NUCs is indefinite. The major drawback of PEG-IFN is its high frequency of adverse events. Some viral genotypes do not show good responses to interferon therapy. Long-term use of NUCs, on the other hand, poses the risk of drug resistance. The ultimate goal of antiviral therapy for CHB is to prevent progression to cirrhosis or HCC via eradication of HBV or persistent viral suppression. The majority of currently treated patients fail to achieve this goal. As indicated above, nucleocapsid assembly is a critical step for HBV genome replication. As the synthesis of viral DNA takes place exclusively within the nucleocapsid, the assembly and disassembly of nucleocapsid must be precisely regulated to ensure correct packaging and release of the viral genome. Nucleocapsid assembly is an evolutionary constraint process that limits the diversity of HBV, and it is highly sensitive to even subtle molecular disturbances. Both assembly and disassembly of nucleocapsid make the process an attractive therapeutic target for the development of new antiviral therapies against various HBV genotypes and drug resistance isolates. A few capsid related anti-HBV compounds have been reported. For example, heteroaryldihydropyrimidines (HAP), including compounds named Bay 41-4109, Bay 38-7690 and Bay 39-5493 (Deres K. et al. Science 2003, 893), and phenylpropenamide derivatives such as AT-61 and AT-130 (Feld J. et al. Antiviral Research 2007, 168-177). Capsid has become a promising drug target with several molecules under clinical stage. There is still a need to develop new treatments for the prophylaxis and treatment of hepatitis B virus infection.

SUMMARY OF THE INVENTION

The present invention relates to novel compounds of formula (I),

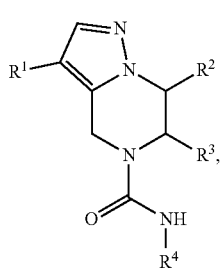

wherein
R¹ is oxooxadiazabicyclo[3.3.1]nonanyl substituted by carboxyC$_{1-6}$alkyl; or
  oxopyrrolidinyl, said oxopyrrolidinyl being once substituted by carboxyC$_{1-6}$alkyl(C$_{1-6}$alkyl)amino, carboxyphenyl, carboxypyridinyl, carboxyphenylamino, halocarboxyphenyl or carboxypyrrolidinyl; or twice substituted by carboxypyrrolidinyl and C$_{1-6}$alkyl;
R² is H or C$_{1-6}$alkyl;
R³ is C$_{1-6}$alkyl;
R⁴ is phenyl, said phenyl being three times substituted by halogen;
  or pharmaceutically acceptable salt, enantiomer or diastereomer thereof.

Objects of the present invention are novel compounds of formula (I), their manufacture, medicaments based on a compound in accordance with the invention and their production as well as the use of compounds of formula (I) as HBV inhibitors and for the treatment or prophylaxis of HBV infection.

DETAILED DESCRIPTION OF THE INVENTION

Definitions

The term "C$_{1-6}$alkyl" denotes a monovalent linear or branched saturated hydrocarbon group of 1 to 6 carbon atoms. In particular embodiments, C$_{1-6}$alkyl has 1 to 6 carbon atoms, and in more particular embodiments 1 to 4 carbon atoms. Examples of C$_{1-6}$alkyl include methyl, ethyl, propyl, isopropyl, n-butyl, iso-butyl, sec-butyl or tert-butyl.

The term "halo" or "halogen" are used interchangeably herein and denote fluoro, chloro, bromo or iodo.

The term "carboxyphenyl" denotes a phenyl group wherein one of the hydrogen atoms of the phenyl group has been replaced by carboxy.

The term "halocarboxyphenyl" denotes a carboxyphenyl group wherein at least one of the hydrogen atoms of the phenyl group has been replaced by halogen. Examples of halocarboxyphenyl are chlorocarboxyphenyl, fluorocarboxyphenyl, difluorocarboxyphenyl and chlorofluorocarboxyphenyl.

The term "oxo" denotes a divalent oxygen atom =O.

The term "diastereomer" denotes a stereoisomer with two or more centers of chirality and whose molecules are not mirror images of one another. Diastereomers have different physical properties, e.g. melting points, boiling points, spectral properties, activities and reactivities.

The term "enantiomers" denotes two stereoisomers of a compound which are non-superimposable mirror images of one another.

The term "pharmaceutically acceptable salts" denotes salts which are not biologically or otherwise undesirable. Pharmaceutically acceptable salts include both acid and base addition salts.

The term "pharmaceutically acceptable acid addition salt" denotes those pharmaceutically acceptable salts formed with inorganic acids such as hydrochloric acid, hydrobromic acid, sulfuric acid, nitric acid, carbonic acid, phosphoric acid, and organic acids selected from aliphatic, cycloaliphatic, aromatic, araliphatic, heterocyclic, carboxylic, and sulfonic classes of organic acids such as formic acid, acetic acid, propionic acid, glycolic acid, gluconic acid, lactic acid, pyruvic acid, oxalic acid, malic acid, maleic acid, maloneic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid, ethanesulfonic acid, p-toluenesulfonic acid, and salicyclic acid.

The term "pharmaceutically acceptable base addition salt" denotes those pharmaceutically acceptable salts formed with an organic or inorganic base. Examples of acceptable inorganic bases include sodium, potassium, ammonium, calcium, magnesium, iron, zinc, copper, manganese, and aluminum salts. Salts derived from pharmaceutically acceptable organic nontoxic bases includes salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperizine, piperidine, N-ethylpiperidine, and polyamine resins.

Compounds of the general formula (I) which contain one or several chiral centers can either be present as racemates, diastereomeric mixtures, or optically active single isomers. The racemates can be separated according to known methods into the enantiomers. Particularly, diastereomeric salts which can be separated by crystallization are formed from the racemic mixtures by reaction with an optically active acid such as e.g. D- or L-tartaric acid, mandelic acid, malic acid, lactic acid or camphorsulfonic acid.

Inhibitor of HBV

The present invention provides (i) novel compounds having the general formula (I),

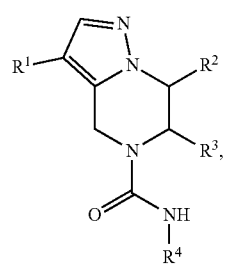

wherein
R¹ is oxooxadiazabicyclo[3.3.1]nonanyl substituted by carboxyC$_{1-6}$alkyl; or
  oxopyrrolidinyl, said oxopyrrolidinyl being once substituted by carboxyC$_{1-6}$alkyl(C$_{1-6}$alkyl)amino, carboxyphenyl, carboxypyridinyl, carboxyphenylamino, halocarboxyphenyl or carboxypyrrolidinyl; or twice substituted by carboxypyrrolidinyl and C$_{1-6}$alkyl;
R² is H or C$_{1-6}$alkyl;
R³ is C$_{1-6}$alkyl;

R⁴ is phenyl, said phenyl being three times substituted by halogen;
or pharmaceutically acceptable salt, enantiomer or diastereomer thereof.

A further embodiment of the present invention is a compound of formula (I), wherein
R¹ is oxooxadiazabicyclo[3.3.1]nonanyl substituted by carboxyC$_{1-6}$alkyl; or
oxopyrrolidinyl, said oxopyrrolidinyl being once substituted by carboxyC$_{1-6}$alkyl(C$_{1-6}$alkyl)amino, carboxyphenyl, carboxyphenylamino, halocarboxyphenyl or carboxypyrrolidinyl; or twice substituted by carboxypyrrolidinyl and C$_{1-6}$alkyl;
R² is H or C$_{1-6}$alkyl;
R³ is C$_{1-6}$alkyl;
R⁴ is phenyl, said phenyl being three times substituted by halogen;
or pharmaceutically acceptable salt, enantiomer or diastereomer thereof.

A further embodiment of the present invention is (ii) a compound of formula (I), wherein
R¹ is carboxymethyl(methyl)aminooxopyrrolidinyl, carboxypyrrolidinyloxopyrrolidinyl, carboxypyrrolidinyl(methyl)oxopyrrolidinyl, carboxyphenyloxopyrrolidinyl, carboxypyridinyloxopyrrolidinyl, carboxyphenylaminooxopyrrolidinyl, fluorocarboxyphenyloxopyrrolidinyl or carboxymethyloxooxadiazabicyclo[3.3.1]nonanyl;
R² is H or methyl;
R³ is methyl;
R⁴ is trifluorophenyl;
or pharmaceutically acceptable salt, enantiomer or diastereomer thereof.

A further embodiment of the present invention is a compound of formula (I), wherein
R¹ is carboxymethyl(methyl)aminooxopyrrolidinyl, carboxypyrrolidinyloxopyrrolidinyl, carboxypyrrolidinyl(methyl)oxopyrrolidinyl, carboxyphenyloxopyrrolidinyl, carboxyphenylaminooxopyrrolidinyl, fluorocarboxyphenyloxopyrrolidinyl or carboxymethyloxooxadiazabicyclo[3.3.1]nonanyl;
R² is H or methyl;
R³ is methyl;
R⁴ is trifluorophenyl;
or pharmaceutically acceptable salt, enantiomer or diastereomer thereof.

In another embodiment of the present invention, particular compounds of the present invention are (iii) selected from:
(2S)-1-[1-[(6S)-6-methyl-5-[(3,4,5-trifluorophenyl)carbamoyl]-6,7-dihydro-4H-pyrazolo[1,5-a]pyrazin-3-yl]-5-oxo-pyrrolidin-3-yl]pyrrolidine-2-carboxylic acid;
(2S)-1-[(2S)-2-methyl-1-[(6S)-6-methyl-5-[(3,4,5-trifluorophenyl)carbamoyl]-6,7-dihydro-4H-pyrazolo[1,5-a]pyrazin-3-yl]-5-oxo-pyrrolidin-3-yl]pyrrolidine-2-carboxylic acid;
2-[methyl-[1-[(6S)-6-methyl-5-[(3,4,5-trifluorophenyl)carbamoyl]-6,7-dihydro-4H-pyrazolo[1,5-a]pyrazin-3-yl]-5-oxo-pyrrolidin-3-yl]amino]acetic acid;
(2R)-1-[(2S)-2-methyl-1-[(6S)-6-methyl-5-[(3,4,5-trifluorophenyl)carbamoyl]-6,7-dihydro-4H-pyrazolo[1,5-a]pyrazin-3-yl]-5-oxo-pyrrolidin-3-yl]pyrrolidine-2-carboxylic acid;
1-[1-[(6S)-6-methyl-5-[(3,4,5-trifluorophenyl)carbamoyl]-6,7-dihydro-4H-pyrazolo[1,5-a]pyrazin-3-yl]-5-oxo-pyrrolidin-3-yl]pyrrolidine-3-carboxylic acid;
(2S)-1-[1-[(6S,7S)-6,7-dimethyl-5-[(3,4,5-trifluorophenyl)carbamoyl]-6,7-dihydro-4H-pyrazolo[1,5-a]pyrazin-3-yl]-5-oxo-pyrrolidin-3-yl]pyrrolidine-2-carboxylic acid;
2-[1-[(6S)-6-methyl-5-[(3,4,5-trifluorophenyl)carbamoyl]-6,7-dihydro-4H-pyrazolo[1,5-a]pyrazin-3-yl]-5-oxo-pyrrolidin-3-yl]benzoic acid;
3-[1-[(6S)-6-methyl-5-[(3,4,5-trifluorophenyl)carbamoyl]-6,7-dihydro-4H-pyrazolo[1,5-a]pyrazin-3-yl]-5-oxo-pyrrolidin-3-yl]benzoic acid;
(2R)-1-[1-[(6S)-6-methyl-5-[(3,4,5-trifluorophenyl)carbamoyl]-6,7-dihydro-4H-pyrazolo[1,5-a]pyrazin-3-yl]-5-oxo-pyrrolidin-3-yl]pyrrolidine-2-carboxylic acid;
3-fluoro-2-[1-[(6S)-6-methyl-5-[(3,4,5-trifluorophenyl)carbamoyl]-6,7-dihydro-4H-pyrazolo[1,5-a]pyrazin-3-yl]-5-oxo-pyrrolidin-3-yl]benzoic acid;
2-fluoro-6-[1-[(6S)-6-methyl-5-[(3,4,5-trifluorophenyl)carbamoyl]-6,7-dihydro-4H-pyrazolo[1,5-a]pyrazin-3-yl]-5-oxo-pyrrolidin-3-yl]benzoic acid;
2-[[1-[(6S)-6-methyl-5-[(3,4,5-trifluorophenyl)carbamoyl]-6,7-dihydro-4H-pyrazolo[1,5-a]pyrazin-3-yl]-5-oxo-pyrrolidin-3-yl]amino]benzoic acid;
2-[7-[(6S)-6-methyl-5-[(3,4,5-trifluorophenyl)carbamoyl]-6,7-dihydro-4H-pyrazolo[1,5-a]pyrazin-3-yl]-6-oxo-3-oxa-7,9-diazabicyclo[3.3.1]nonan-9-yl]acetic acid;
4-fluoro-2-[1-[(6S)-6-methyl-5-[(3,4,5-trifluorophenyl)carbamoyl]-6,7-dihydro-4H-pyrazolo[1,5-a]pyrazin-3-yl]-5-oxo-pyrrolidin-3-yl]benzoic acid;
5-fluoro-2-[1-[(6S)-6-methyl-5-[(3,4,5-trifluorophenyl)carbamoyl]-6,7-dihydro-4H-pyrazolo[1,5-a]pyrazin-3-yl]-5-oxo-pyrrolidin-3-yl]benzoic acid;
4-[1-[(6S)-6-methyl-5-[(3,4,5-trifluorophenyl)carbamoyl]-6,7-dihydro-4H-pyrazolo[1,5-a]pyrazin-3-yl]-5-oxo-pyrrolidin-3-yl]benzoic acid;
6-[1-[(6S)-6-methyl-5-[(3,4,5-trifluorophenyl)carbamoyl]-6,7-dihydro-4H-pyrazolo[1,5-a]pyrazin-3-yl]-5-oxo-pyrrolidin-3-yl]pyridine-2-carboxylic acid; and
2-[1-[(6S)-6-methyl-5-[(3,4,5-trifluorophenyl)carbamoyl]-6,7-dihydro-4H-pyrazolo[1,5-a]pyrazin-3-yl]-5-oxo-pyrrolidin-3-yl]pyridine-3-carboxylic acid.

Synthesis

The compounds of the present invention can be prepared by any conventional means. Suitable processes for synthesizing these compounds as well as their starting materials are provided in the schemes below and in the examples. All substituents, in particular, R¹ to R⁴ are as defined above unless otherwise indicated. Furthermore, and unless explicitly otherwise stated, all reactions, reaction conditions, abbreviations and symbols have the meanings well known to a person of ordinary skill in organic chemistry.

Scheme 1:

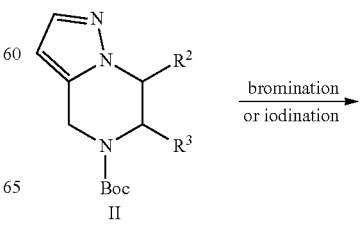

-continued

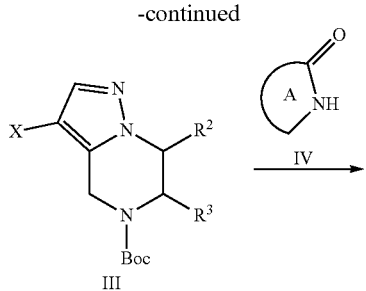

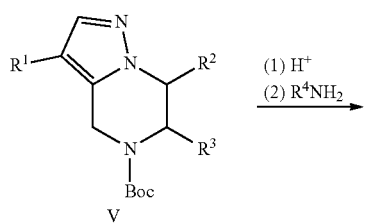

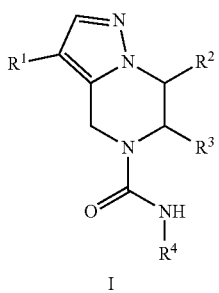

Compound of formula IV (ring A) is oxooxadiazabicyclo [3.3.1]nonane substituted by carboxyC$_{1-6}$alkyl; or oxopyrrolidine, said oxopyrrolidine being once substituted by carboxyC$_{1-6}$alkyl(C$_{1-6}$alkyl)amino, carboxyphenyl, carboxyphenylamino, halocarboxyphenyl or carboxypyrrolidinyl, or twice substituted by carboxypyrrolidinyl and C$_{1-6}$alkyl. X is bromo or iodo.

As depicted in Scheme 1, the synthesis of compounds of the present invention could be started from bicyclic compound of formula (II), which was treated with halogenating agents, such as N-iodosuccinimide or N-bromosuccinimide, to give compound of formula (III). Coupling reaction between compound of formula (III) and compound of formula (IV) in the presence of copper catalyst, such as CuI, afforded compound of formula (V). The following Boc-deprotection in an acidic condition such as HCl/EtOAc or TFA/DCM and urea formation with amine R$^3$NH$_2$ in the presence of a phosgene equivalent, such as triphosgene and carbonyldiimidazole could afford final compound of formula (I). In the aforementioned urea formation reaction, a suitable isocyanate or phenyl carbamate was also applied (Padiya, K. J. et al. *Org Lett.* 2012, 14, 2814 and references cited therein).

This invention also relates to a process for the preparation of a compound of formula (I) comprising the following reaction:

(a) the reaction of compound of formula (V),

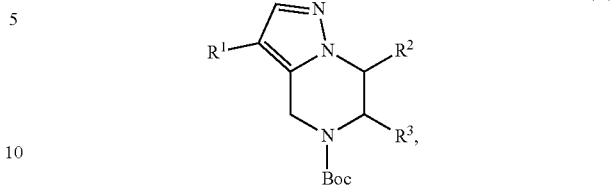

with an acid followed by urea formation with amine R$^4$NH$_2$ in the presence of a phosgene equivalent; wherein R$^1$ and R$^4$ are defined above.

In step (a), the acid can be for example HCl/EtOAc and TFA/DCM; phosgene equivalent can be for example triphosgene and carbonyldiimidazole.

A compound of formula (I) when manufactured according to the above process is also an object of the invention.

Pharmaceutical Compositions and Administration

Another embodiment provides pharmaceutical compositions or medicaments containing the compounds of the invention and a therapeutically inert carrier, diluent or excipient, as well as methods of using the compounds of the invention to prepare such compositions and medicaments. In one example, compounds of formula (I) may be formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but preferably ranges anywhere from about 3 to about 8. In one example, a compound of formula (I) is formulated in an acetate buffer, at pH 5. In another embodiment, the compounds of formula (I) are sterile. The compound may be stored, for example, as a solid or amorphous composition, as a lyophilized formulation or as an aqueous solution.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "effective amount" of the compound to be administered will be governed by such considerations, and is the minimum amount necessary to the suppression of serum HBV DNA levels, or HBeAg seroconversion to HBeAb, or HBsAg loss, or normalization of alanine aminotransferase levels and improvement in liver histology. For example, such amount may be below the amount that is toxic to normal cells, or the mammal as a whole.

In one example, the pharmaceutically effective amount of the compound of the invention administered parenterally per dose will be in the range of about 0.01 to 100 mg/kg, alternatively about 0.1 to 20 mg/kg of patient body weight per day, with the typical initial range of compound used being 0.3 to 15 mg/kg/day. In another embodiment, oral unit dosage forms, such as tablets and capsules, contain from about 0.1 to about 1000 mg of the compound of the invention.

The compounds of the invention may be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, or subcutaneous administration.

The compounds of the present invention may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents.

A typical formulation is prepared by mixing a compound of the present invention and a carrier or excipient. Suitable carriers and excipients are well known to those skilled in the art and are described in detail in, e.g., Ansel, Howard C., et al., *Ansel's Pharmaceutical Dosage Forms and Drug Delivery Systems*. Philadelphia: Lippincott, Williams & Wilkins, 2004; Gennaro, Alfonso R., et al. *Remington: The Science and Practice of Pharmacy*. Philadelphia: Lippincott, Williams & Wilkins, 2000; and Rowe, Raymond C. *Handbook of Pharmaceutical Excipients*. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

An example of a suitable oral dosage form is a tablet containing about 0.1 mg to 1000 mg of the compound of the invention compounded with about 30 mg to 90 mg anhydrous lactose, about 5 mg to 40 mg sodium croscarmellose, about 5 mg to 30 mg polyvinylpyrrolidone (PVP) K30, and about 1 mg to 10 mg magnesium stearate. The powdered ingredients are first mixed together and then mixed with a solution of the PVP. The resulting composition can be dried, granulated, mixed with the magnesium stearate and compressed to tablet form using conventional equipment. An example of an aerosol formulation can be prepared by dissolving the compound, for example 5 mg to 400 mg, of the invention in a suitable buffer solution, e.g. a phosphate buffer, adding a tonicifier, e.g. a salt such sodium chloride, if desired. The solution may be filtered, e.g., using a 0.2 micron filter, to remove impurities and contaminants.

An embodiment, therefore, includes a pharmaceutical composition comprising a compound of formula (I), or a stereoisomer or pharmaceutically acceptable salt thereof. In a further embodiment includes a pharmaceutical composition comprising a compound of formula (I), or a stereoisomer or pharmaceutically acceptable salt thereof, together with a pharmaceutically acceptable carrier or excipient.

Indications and Methods of Treatment

The compounds of the invention can inhibit HBV's DNA synthesis and reduce HBV DNA levels. Accordingly, the compounds of the invention are useful for the treatment or prophylaxis of HBV infection.

The invention relates to the use of a compound of formula (I) for the treatment or prophylaxis of HBV infection.

The use of a compound of formula (I) for the preparation of medicaments useful in the treatment or prophylaxis diseases that are related to HBV infection is an object of the invention.

The invention relates in particular to the use of a compound of formula (I) for the preparation of a medicament for the treatment or prophylaxis of HBV infection.

Another embodiment includes a method for the treatment or prophylaxis of HBV infection which method comprises administering an effective amount of a compound of formula (I), a stereoisomer, tautomer, prodrug or pharmaceutically acceptable salt thereof.

EXAMPLES

The invention will be more fully understood by reference to the following examples. They should not, however, be construed as limiting the scope of the invention.

Abbreviations used herein are as follows:
CbzCl: benzyl chloroformate
DCE: 1,2-dichloroethylene
DIAD: diisopropyl azodicarboxylate
DIPEA: N,N-diisopropylethylamine
EA or EtOAc: ethyl acetate
$EC_{50}$: half maximal effective concentration
HPLC: high performance liquid chromatography
LCMS: liquid chromatography-mass spectrometry
MS: mass spectrometry
MsCl: methanesulfonyl chloride
NIS: N-iodosuccinimide
PE: petroleum ether
prep-HPLC: preparative high performance liquid chromatography
prep-TLC: preparative thin layer chromatography
psi: pounds per square inch
SFC: supercritical fluid chromatography
TEA: trimethylamine
t-BuXPhos: 2-di-tert-butylphosphino-2',4',6'-triisopropyl-biphenyl
TMG: 1,1,3,3-tetramethylguanidine
$Pd_2(dba)_3$: Tris(dibenzylideneacetone)dipalladium(0)
pgRNA: pre-genomic RNA
qPCR: quantitative polymerase chain reaction
v/v volume ratio General Experimental Conditions Intermediates and final compounds were purified by flash chromatography using one of the following instruments: i) Biotage SP1 system and the Quad 12/25 Cartridge module. ii) ISCO combi-flash chromatography instrument. Silica gel Brand and pore size: i) KP-SIL 60 Å, particle size: 40-60 µM; ii) CAS registry NO: Silica Gel: 63231-67-4, particle size: 47-60 micron silica gel; iii) ZCX from Qingdao Haiyang Chemical Co., Ltd, pore: 200-300 or 300-400.

Intermediates and final compounds were purified by preparative HPLC on reversed phase column using X Bridge™ Perp $C_{18}$ (5 µm, OBD™ 30×100 mm) column or SunFire™ Perp $C_{18}$ (5 µm, OBD™ 30×100 mm) column. Waters AutoP purification System (Column: XBridge™ Prep-C18, 30×100 mm, Sample Manager 2767, Pump 2525, Detector: Micromass ZQ and UV 2487, solvent system: acetonitrile and 0.1% ammonium hydroxide in water).

LC/MS spectra of compounds were obtained using a LC/MS (Waters™ Alliance 2795-Micromass ZQ). LC/MS conditions were as follows (running time 6 mins):

Acidic condition: A: 0.1% formic acid in $H_2O$: B: 0.1% formic acid in acetonitrile;

Basic condition: A: 0.1% $NH_3.H_2O$ in $H_2O$; B: acetonitrile;

Neutral condition: A: $H_2O$: B: acetonitrile.

Mass spectra (MS): generally only ions which indicate the parent mass are reported, and unless otherwise stated the mass ion quoted is the positive mass ion (M+H)⁺.

The microwave assisted reactions were carried out in a Biotage Initiator Sixty or CEM Discover.

NMR Spectra, were obtained using Bruker Avance 400 MHz.

All reactions involving air-sensitive reagents were performed under an argon atmosphere. Reagents were used as received from commercial suppliers without further purification unless otherwise noted.

The following examples are intended to illustrate the meaning of the present invention but should by no means represent a limitation within the meaning of the present invention.

Preparative Examples

The invention will be more fully understood by reference to the following examples. They should not, however, be construed as limiting the scope of the invention.

Intermediate I-1 tert-Butyl (6S)-3-iodo-6-methyl-6,7-dihydro-4H-pyrazolo[1,5-a]pyrazine-5-carboxylate

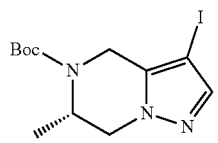 [SMILES: C[C@H]1Cn2ncc(I)c2CN1C(=O)OC(C)(C)C]

Intermediate I-1 was prepared according to the following scheme:

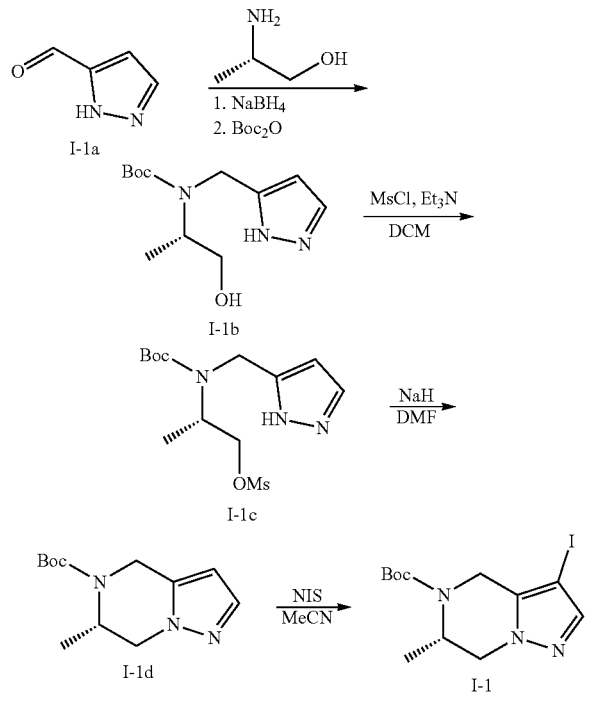

Step 1: Preparation of tert-butyl N-[(1S)-2-hydroxy-1-methyl-ethyl]-N-(1H-pyrazol-5-ylmethyl)carbamate (Compound I-1b)

To a solution of 1H-pyrazole-5-carbaldehyde (compound I-1a, 54.0 g, 562.5 mmol) in MeOH (300 mL) was added (2S)-2-aminopropan-1-ol (41.2 g, 675 mmol) and the reaction mixture was stirred at 25° C. for 1 hour. NaBH₄ (25.9 g, 675.0 mmol) was added at 0° C. and the reaction mixture was stirred for another 1 hour followed by the addition of H₂O (300 mL) and Boc₂O (147.1 g, 675.0 mmol). The resulting mixture was stirred at room temperature for 12 hours, and extracted with EtOAc (600 mL). The organic layer was dried over Na₂SO₄, filtered and concentrated. The residue was purified by column chromatography (eluting with 0%~5% MeOH in DCM) to afford compound I-1b (80 g) as a colorless oil. LCMS (M+H⁺): 334.

Step 2: Preparation of [(2S)-2-[tert-butoxycarbonyl(1H-pyrazol-5-ylmethyl)amino]propyl] methanesulfonate (Compound I-1c)

To a mixture of tert-butyl N-[(1S)-2-hydroxy-1-methyl-ethyl]-N-(1H-pyrazol-5-ylmethyl)carbamate (compound I-1b, 80.0 g, 117.2 mmol) and Et₃N (100.5 g, 995.6 mmol) in DCM (800 mL) was added MsCl (57.3 g, 497.8 mmol) slowly at 0° C. The resulting mixture was stirred at room temperature for 2 hours, then washed with water (500 mL), brine (500 mL), and dried over Na₂SO₄. The organic layer was concentrated to afford compound I-1c (100 g, crude), which was used directly in next step.

Step 3: Preparation of tert-butyl (6S)-6-methyl-6,7-dihydro-4H-pyrazolo[1,5-a]pyrazine-5-carboxylate (Compound I-1d)

To a solution of [(2S)-2-[tert-butoxycarbonyl(1H-pyrazol-5-ylmethyl)amino]propyl]methanesulfonate (compound I-1c, 100.0 g, 313.4 mmol) in DMF (1000 mL) was added NaH (15.0 g, 376.2 mmol) in portions at 0° C. The reaction mixture was then stirred at room temperature for 12 hours, poured into water (2000 mL) and extracted with EtOAc (1000 mL) twice. The combined organic layer was concentrated, and the residue was purified by column chromatography (eluting with 10%-80% EtOAc in petroleum ether) to afford compound I-1d (18.0 g) as a colorless oil. LCMS (M+H⁺): 238.

Step 4: Preparation of tert-butyl (6S)-3-iodo-6-methyl-6,7-dihydro-4H-pyrazolo[1,5-a]pyrazine-5-carboxylate (intermediate I-1)

To a solution of tert-butyl 6-methyl-6,7-dihydro-4H-pyrazolo[1,5-a]pyrazine-5-carboxylate (compound 53c, 3.3 g, 14.8 mmol) in CH₃CN (40 mL) was added NIS (5.0 g, 22.1 mmol) slowly.

The reaction mixture was stirred at room temperature for 16 hours and then extracted with EtOAc (50 mL), washed with brine (50 mL). The organic layer was dried over Na₂SO₄ and concentrated, and the residue was purified by column chromatography (eluting with 10%-80% EtOAc in petroleum ether) to afford intermediate I-1 (4.8 g) as a white solid.

Intermediate I-2 tert-Butyl (6S,7S)-3-iodo-6,7-dimethyl-6,7-dihydro-4H-pyrazolo[1,5-a]pyrazine-5-carboxylate

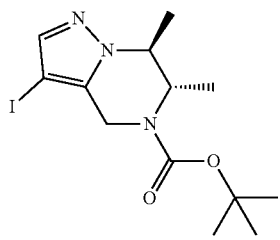 [SMILES: C[C@H]1[C@H](C)n2ncc(I)c2CN1C(=O)OC(C)(C)C]

Intermediate I-2 was prepared according to the following scheme:

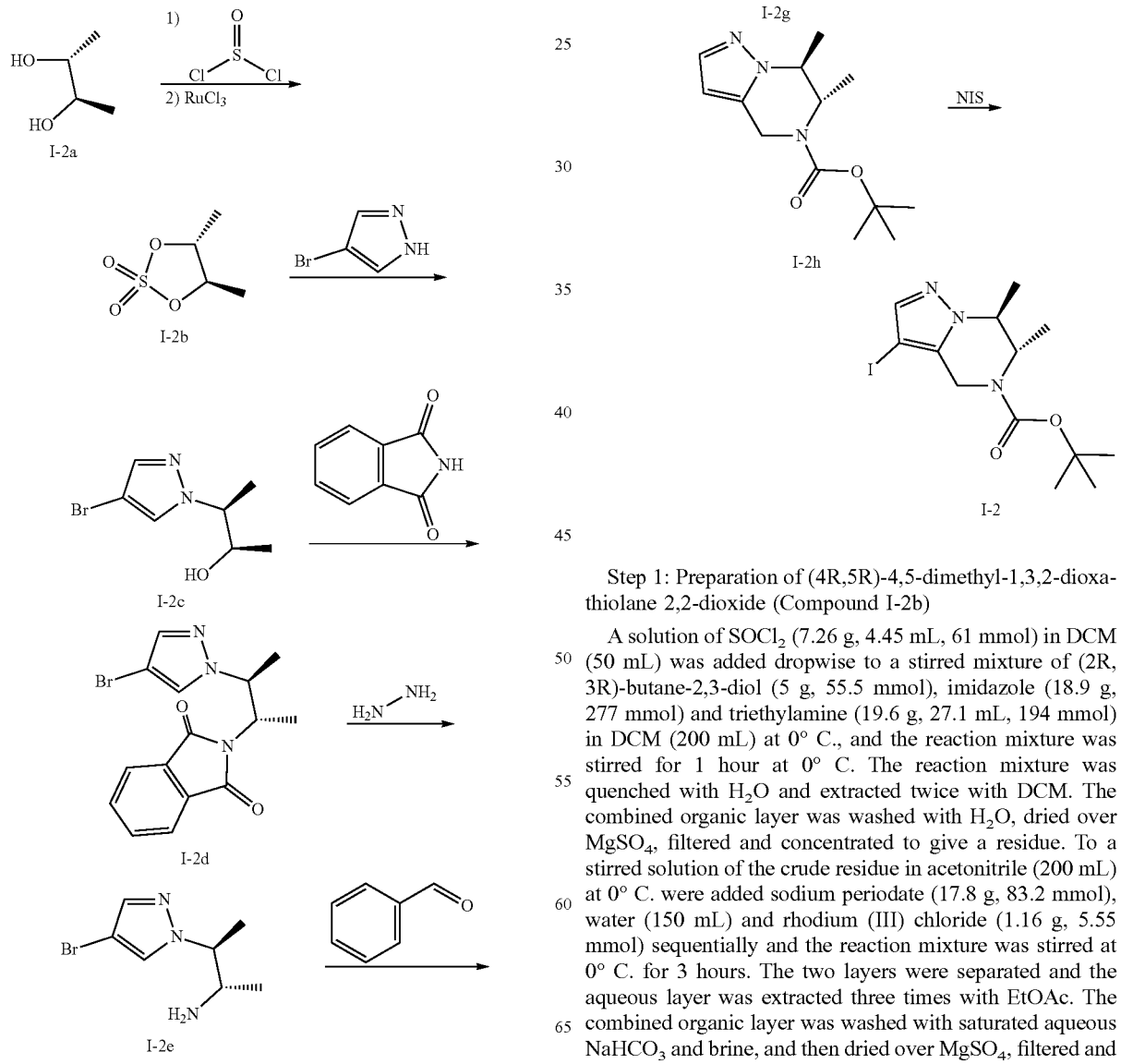

Step 1: Preparation of (4R,5R)-4,5-dimethyl-1,3,2-dioxathiolane 2,2-dioxide (Compound I-2b)

A solution of $SOCl_2$ (7.26 g, 4.45 mL, 61 mmol) in DCM (50 mL) was added dropwise to a stirred mixture of (2R,3R)-butane-2,3-diol (5 g, 55.5 mmol), imidazole (18.9 g, 277 mmol) and triethylamine (19.6 g, 27.1 mL, 194 mmol) in DCM (200 mL) at 0° C., and the reaction mixture was stirred for 1 hour at 0° C. The reaction mixture was quenched with $H_2O$ and extracted twice with DCM. The combined organic layer was washed with $H_2O$, dried over $MgSO_4$, filtered and concentrated to give a residue. To a stirred solution of the crude residue in acetonitrile (200 mL) at 0° C. were added sodium periodate (17.8 g, 83.2 mmol), water (150 mL) and rhodium (III) chloride (1.16 g, 5.55 mmol) sequentially and the reaction mixture was stirred at 0° C. for 3 hours. The two layers were separated and the aqueous layer was extracted three times with EtOAc. The combined organic layer was washed with saturated aqueous $NaHCO_3$ and brine, and then dried over $MgSO_4$, filtered and concentrated to give compound I-2b as a colorless oil (8 g).

Step 2: Preparation of (2R,3S)-3-(4-bromo-1H-pyrazol-1-yl)butan-2-ol (Compound I-2c)

A mixture of (4R,5R)-4,5-dimethyl-1,3,2-dioxathiolane 2,2-dioxide (compound I-2b, 8 g, 52.6 mmol), 4-bromo-1H-pyrazole (11.6 g, 78.9 mmol) and $Cs_2CO_3$ (34.3 g, 105 mmol) in DMF (50 mL) was stirred at room temperature for 16 hours. The reaction mixture was filtered and concentrated. The resulting residue was taken up in 400 mL of THF/50% aq. $H_2SO_4$ (v/v 1/2), and stirred vigorously for 48 hours. The reaction mixture was then carefully basified with 10 M aqueous NaOH solution, and the layers were separated. The aqueous layer was extracted twice with DCM, and the combined organic layer was washed with brine, dried over $MgSO_4$, filtered and concentrated to give compound I-2c as a colorless oil (8 g). LCMS (M+H$^+$): 219

Step 3: Preparation of 2-((2S,3S)-3-(4-bromo-1H-pyrazol-1-yl)butan-2-yl)isoindoline-1,3-dione (Compound I-2d)

To a mixture of (2R,3S)-3-(4-bromo-1H-pyrazol-1-yl)butan-2-ol (compound I-2c, 8 g, 36.5 mmol), isoindoline-1,3-dione (5.91 g, 40.2 mmol) and triphenylphosphine (12.5 g, 47.5 mmol) in THF (75 mL) was added DIAD (11.1 g, 54.8 mmol) dropwise at room temperature. Then the reaction mixture was stirred at room temperature for 2 hours, and concentrated in vacuo. The crude product was purified by flash chromatography (silica gel, 0% to 50% EtOAc in hexanes) to give compound I-2d as a white solid (5 g). LCMS (M+H$^+$): 348

Step 4: Preparation of (2S,3S)-3-(4-bromo-1H-pyrazol-1-yl)butan-2-amine (Compound I-2e)

A mixture of 2-((2S,3S)-3-(4-bromo-1H-pyrazol-1-yl)butan-2-yl)isoindoline-1,3-dione (compound I-2d, 5 g, 14.4 mmol) and Hydrazine hydrate (7.19 g, 144 mmol) in MeOH (50 mL) was stirred at 80° C. for 15 hours. The reaction mixture was concentrated in vacuo. The residue was dissolved in DCM, the solid was filtered off and the filtrate was concentrated to give compound I-2e as a slight yellow oil (3 g). LCMS (M+H$^+$): 218

Step 5: Preparation of (2S,3S)—N-benzyl-3-(4-bromo-1H-pyrazol-1-yl)butan-2-amine (Compound I-2f)

A mixture of (2S,3S)-3-(4-bromo-1H-pyrazol-1-yl)butan-2-amine (compound I-2e, 3 g, 13.8 mmol) and benzaldehyde (1.61 g, 15.1 mmol) in MeOH (50 mL) was stirred for 2 hours at room temperature. Then sodium borohydride (624 mg, 16.5 mmol) was added slowly at 0° C. in 30 mins and the reaction mixture was stirred at room temperature for another 30 mins. The reaction mixture was poured into 100 mL of $H_2O$ and extracted with EtOAc (100 mL) twice. The combined organic layer was dried over $Na_2SO_4$ and then concentrated in vacuo. The crude product was purified by flash chromatography (silica gel, 0% to 50% EtOAc in hexanes) to give compound I-2f as light yellow oil (4 g). LCMS (M+H$^+$): 308

Step 6: Preparation of (6S,7S)-5-benzyl-3-bromo-6,7-dimethyl-4,5,6,7-tetrahydropyrazolo[1,5-a]pyrazine (Compound I-2g)

To a stirred solution of (2S,3S)—N-benzyl-3-(4-bromo-1H-pyrazol-1-yl)butan-2-amine (compound I-2f, 4 g, 13 mmol) in acetonitrile (50 mL) was added paraformaldehyde (1.95 g, 64.9 mmol) and 2,2,2-trifluoroacetic acid (296 mg, 2.6 mmol), and the reaction mixture was stirred at 70° C. for 6 hours. The reaction mixture was concentrated and the residue was then taken up in EtOAc, and washed with $NaHCO_3$ aq. solution and brine. The organic layer was concentrated and the residue was purified on a silica gel column (heptane: EtOAc 1:0 to 9:1) to give compound I-2g as a colorless oil (2.3 g). LCMS (M+H$^+$): 320

Step 7: Preparation of tert-butyl (6S,7S)-6,7-dimethyl-6,7-dihydro-4H-pyrazolo[1,5-a]pyrazine-5-carboxylate (Compound I-2h)

A mixture of (6S,7S)-5-benzyl-3-bromo-6,7-dimethyl-4,5,6,7-tetrahydropyrazolo[1,5-a]pyrazine (compound I-2g, 1.5 g, 4.68 mmol), di-tert-butyl dicarbonate (2.18 mL, 9.37 mmol) and Pd(OH)$_2$/C (329 mg) in MeOH (50 mL) was heated to 50° C. and stirred for 15 h under hydrogen. Then the solid was filtered off and the filtrate was concentrated. The residue was dissolved in THF/MeOH (v/v 5:1, 50 ml), di-tert-butyl dicarbonate (2.18 ml, 9.37 mmol) and $Na_2CO_3$ (496 mg, 4.68 mmol) were added. The reaction mixture was stirred at room temperature for 16 hours and then filtered through celite, the filtrate was concentrated and the crude material was purified by flash chromatography (silica gel, 10% to 50% EtOAc in hexanes, EtOAc contain 10% MeOH). LCMS (M+H$^+$): 252.

Step 8: Preparation of tert-butyl (6S,7S)-3-iodo-6,7-dimethyl-6,7-dihydro-4H-pyrazolo[1,5-a]pyrazine-5-carboxylate (Intermediate I-2)

To a solution of (6S,7S)-tert-butyl 6,7-dimethyl-6,7-dihydropyrazolo[1,5-a]pyrazine-5(4H)-carboxylate (compound I-2h, 1.2 g, 4.77 mmol) in MeCN (20 mL) was added NIS (1.61 g, 7.16 mmol) and then stirred at room temperature for 16 hours. The reaction mixture was quenched with aq. $NaHSO_3$, extracted with EtOAc, dried and concentrated, The crude material was purified by flash chromatography (silica gel, 0% to 50% EtOAc in hexanes) to give intermediate I-2 as colorless oil, 1.2 g. LCMS (M+H$^+$): 378.

Intermediate I-3

Phenyl N-(3,4,5-trifluorophenyl)carbamate

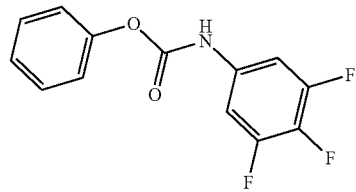 [SMILES: O=C(Nc1cc(F)c(F)c(F)c1)Oc1ccccc1]

Intermediate I-3 was prepared according to the following scheme:

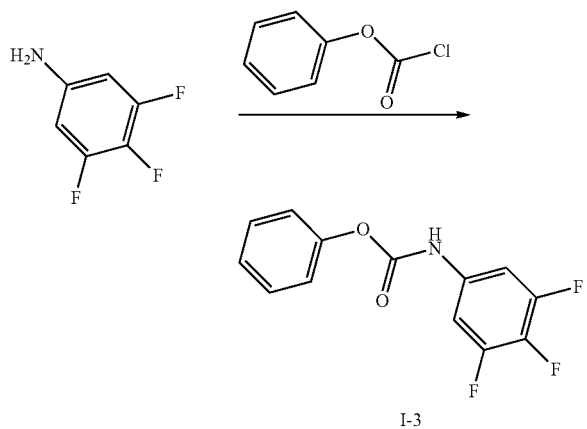

I-3

To a solution of 3,4,5-trifluoroaniline (1.47 g, 10 mmol) in DCM (30 mL) was added DIPEA (2.06 mL, 12 mmol), followed by adding phenyl chloroformate (1.38 mL, 11 mmol) dropwise at 0° C. After addition the reaction mixture was warmed to room temperature and stirred overnight. The reaction mixture was diluted with DCM, washed with water. The organic phase was separated, dried over $Na_2SO_4$ and concentrated. The residue was purified by column to give intermediate I-3 as a white solid, 1.87 g. LCMS $(M+H^+)$: 268.

Example 1

(2S)-1-[1-[(6S)-6-methyl-5-[(3,4,5-trifluorophenyl)carbamoyl]-6,7-dihydro-4H-pyrazolo[1,5-a]pyrazin-3-yl]-5-oxo-pyrrolidin-3-yl]pyrrolidine-2-carboxylic acid

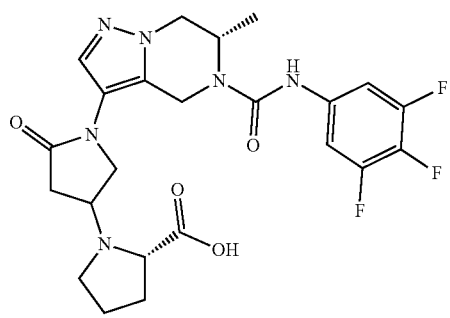 [SMILES: C[C@H]1Cn2ncc(N3CC(N4CCC[C@H]4C(=O)O)CC3=O)c2CN1C(=O)Nc1cc(F)c(F)c(F)c1]

The title compound was prepared according to the following scheme:

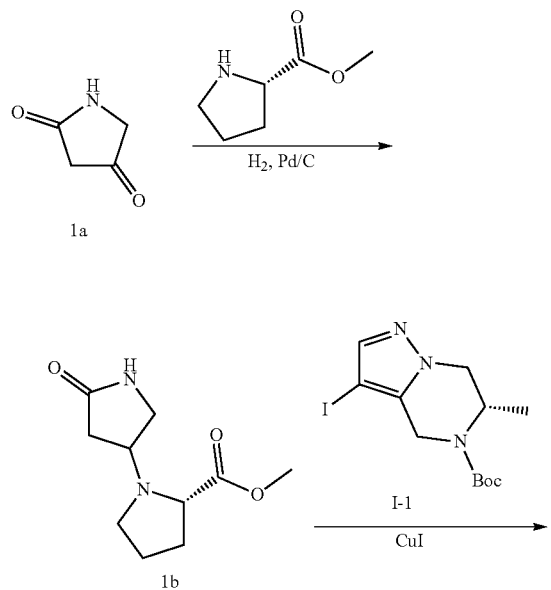

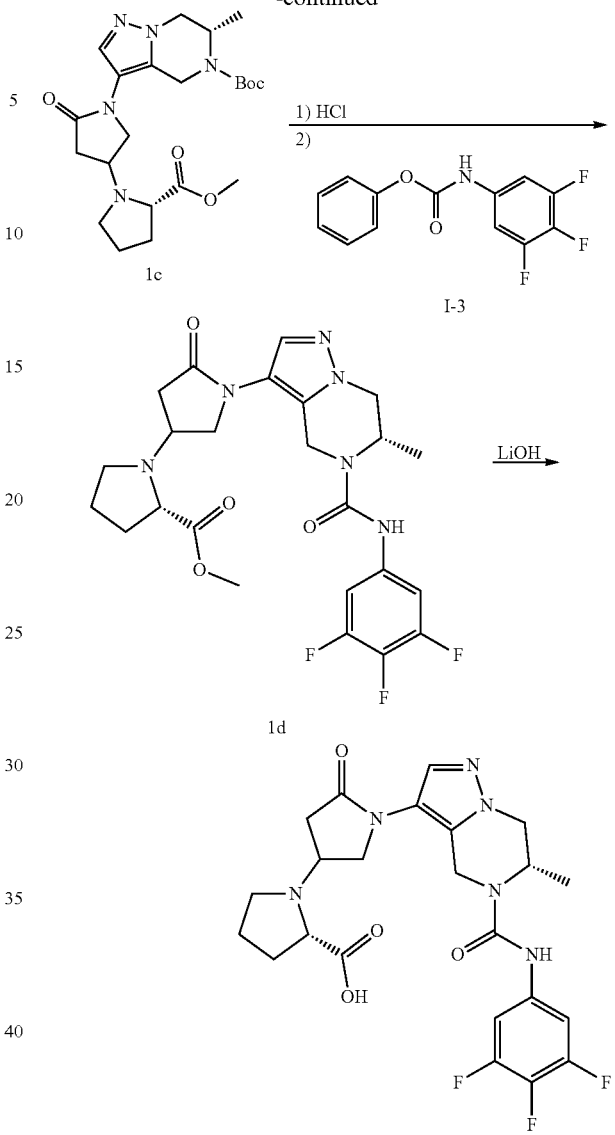

Step 1: Preparation of methyl (2S)-1-(5-oxopyrrolidin-3-yl)pyrrolidine-2-carboxylate (Compound 1b)

A mixture of pyrrolidine-2,4-dione (compound 1a, 200 mg, 2.02 mmol), methyl (2S)-pyrrolidine-2-carboxylate (334 mg, 2.02 mmol) and Pd/C (100 mg) in MeOH (20 mL) was stirred at room temperature for 40 hours under 50 psi $H_2$ atmosphere. The reaction mixture was filtered and the filtrate was concentrated to give compound 1b (400 mg, crude) as a brown oil.

Step 2: Preparation of tert-butyl (6S)-3-[4-[(2S)-2-methoxycarbonylpyrrolidin-1-yl]-2-oxo-pyrrolidin-1-yl]-6-methyl-6,7-dihydro-4H-pyrazol[1,5-a]pyrazine-5-carboxylate (Compound 1c)

A mixture of methyl (2S)-1-(5-oxopyrrolidin-3-yl)pyrrolidine-2-carboxylate (compound 1b, 400 mg), tert-butyl (6S)-3-iodo-6-methyl-6,7-dihydro-4H-pyrazolo[1,5-a]pyrazine-5-carboxylate (Intermediate I-1, 684 mg, 1.88 mmol), (1R,2R)—N1,N2-dimethylcyclohexane-1,2-diamine (54 mg, 0.38 mmol), CuI (72 mg, 0.38 mmol) and $K_3PO_4$ (800 mg, 3.78 mmol) in dioxane (20 mL) was degassed and refilled with $N_2$, and stirred at 110° C. under $N_2$ for 16 hours. The reaction mixture was filtered, the filtrate was concentrated and the crude product was purified by prep-HPLC to give compound 1c (200 mg) as a white solid. LCMS (M+H⁺): 448.3.

Step 3: Preparation of methyl (2S)-1-[1-[(6S)-6-methyl-5-[(3,4,5-trifluorophenyl)carbamoyl]-6,7-dihydro-4H-pyrazolo[1,5-a]pyrazin-3-yl]-5-oxo-pyrrolidin-3-yl]pyrrolidine-2-carboxylate (Compound 1d)

To a solution of tert-butyl (6S)-3-[4-[(2S)-2-methoxycarbonylpyrrolidin-1-yl]-2-oxo-pyrrolidin-1-yl]-6-methyl-6,7-dihydro-4H-pyrazolo[1,5-a]pyrazine-5-carboxylate (compound 1c, 200 mg, 0.447 mmol) in MeOH (10 mL) was added a solution of HCl in MeOH (4M, 5 mL, 20 mmol). The reaction mixture was stirred at room temperature for 2 h, and then concentrated to give a crude material (0.18 g) as a brown solid. The solid was dissolved in DMF (4 mL), to which were added DIPEA (0.16 g, 1.18 mmol) and phenyl N-(3,4,5-trifluorophenyl)carbamate (Intermediate I-3, 0.15 g, 0.56 mmol). The reaction mixture was stirred at 30° C. for 12 h, diluted with H₂O (20 mL), and extracted three times with EtOAc (20 mL each). The combined organic phase was concentrated and the obtained residue was purified by prep-TLC (DCM/MeOH=10/1) to give compound 1d (0.15 g) as a brown solid. LCMS (M+H⁺): 521.4

Step 4: Preparation of (2S)-1-[1-[(6S)-6-methyl-5-[(3,4,5-trifluorophenyl)carbamoyl]-6,7-dihydro-4H-pyrazolo[1,5-a]pyrazin-3-yl]-5-oxo-pyrrolidin-3-yl]pyrrolidine-2-carboxylic acid (Example 1)

To a mixture of methyl (2S)-1-[1-[(6S)-6-methyl-5-[(3,4,5-trifluorophenyl)carbamoyl]-6,7-dihydro-4H-pyrazolo[1,5-a]pyrazin-3-yl]-5-oxo-pyrrolidin-3-yl]pyrrolidine-2-carboxylate (compound 1d, 150 mg, 0.28 mmol) in MeOH (2 mL) and H₂O (1 mL) was added LiOH (28 mg, 1.15 mmol), the reaction mixture was stirred at room temperature for 2 h, then acidified with 2 M aqueous HCl solution to pH=5, and concentrated. The obtained residue was purified by prep-HPLC to give Example 1 (30 mg) as a white solid. LCMS (M+H⁺): 507.2, ¹H NMR (400 MHz, METHANOL-d₄) δ ppm 7.71-7.61 (m, 1H), 7.40-7.24 (m, 2H), 5.15-5.05 (m, 1H), 5.05-4.92 (m, 1H), 4.58-4.45 (m, 1H), 4.40-3.90 (m, 6H), 3.90-3.75 (m, 1H), 3.26-3.15 (m, 1H), 3.15-2.85 (m, 2H), 2.56-2.42 (m, 1H), 2.31-2.20 (m, 1H), 2.20-2.04 (m, 1H), 2.04-1.88 (m, 1H), 1.32-1.24 (m, 3H)

Example 2

(2S)-1-[(2S)-2-methyl-1-[(6S)-6-methyl-5-[(3,4,5-trifluorophenyl)carbamoyl]-6,7-dihydro-4H-pyrazolo[1,5-a]pyrazin-3-yl]-5-oxo-pyrrolidin-3-yl]pyrrolidine-2-carboxylic acid

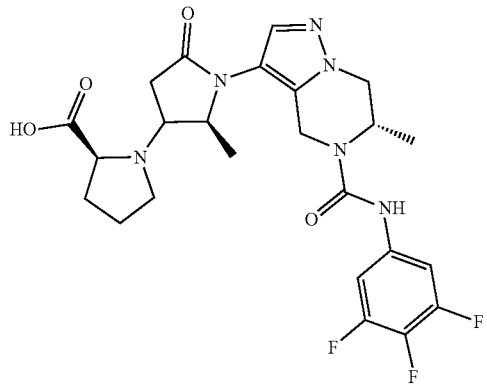 [SMILES: C[C@H]1Cn2ncc(N3C(=O)CC(N4CCC[C@H]4C(=O)O)[C@@H]3C)c2CN1C(=O)Nc1cc(F)c(F)c(F)c1]

The title compound was prepared according to the following scheme:

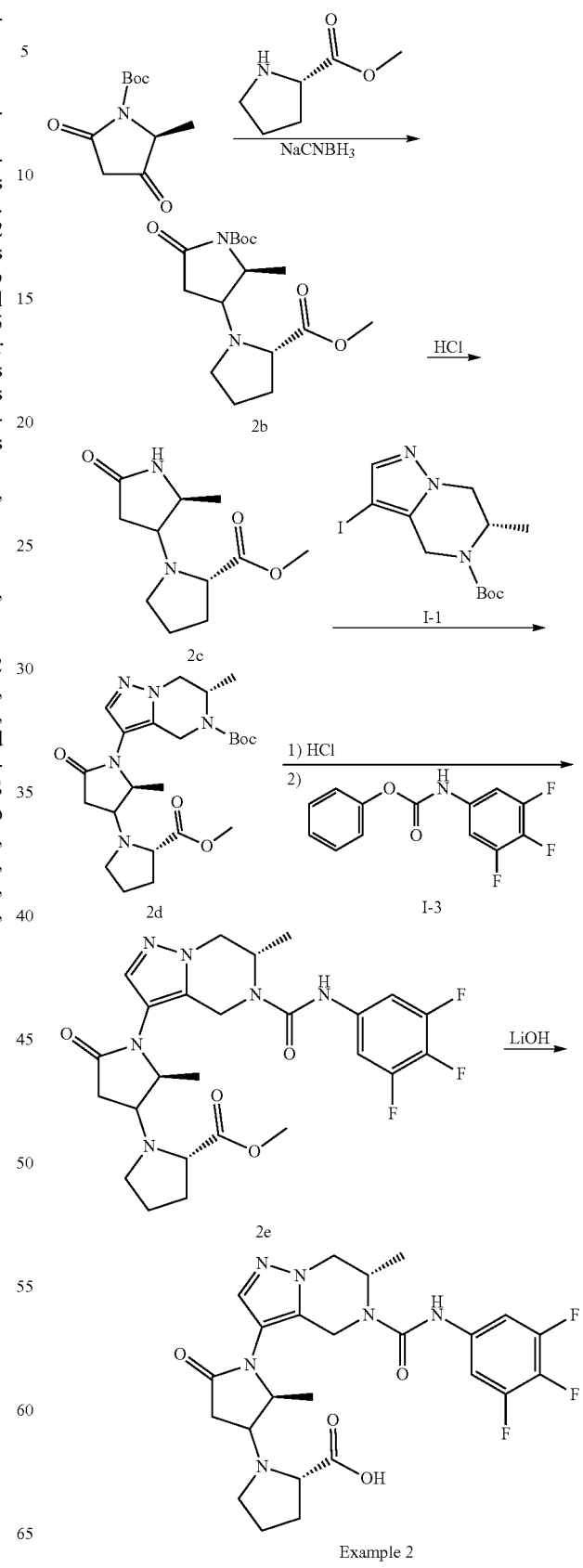

Step 1: Preparation of tert-butyl (2S)-3-[(2S)-2-methoxycarbonylpyrrolidin-1-yl]-2-methyl-5-oxo-pyrrolidine-1-carboxylate (Compound 2b)

To the mixture of tert-butyl (2S)-2-methyl-3,5-dioxopyrrolidine-1-carboxylate (500 mg, 2.34 mmol, for its synthesis, refer to Hosseini, M. et al Org. Letters 2006, 8, 2103) in DCE (10 mL) was added methyl (2S)-pyrrolidine-2-carboxylate (395 mg, 2.81 mmol) and AcOH (5 drops), the reaction mixture was stirred for 5 hours at 40° C., then NaCNBH$_3$ (294 mg, 4.68 mmol) was added. The reaction mixture was stirred at 40° C. for 12 hours and then diluted with EtOAc (100 mL), filtered, and the filtrate was concentrated, the residue was purified by column chromatography (PE/EtOAc=1/1) to give crude compound 2b (1.2 g, crude) as a colorless oil.

Step 2: Preparation of methyl (2S)-1-[(2S)-2-methyl-5-oxo-pyrrolidin-3-yl]pyrrolidine-2-carboxylate (Compound 2c)

To a mixture of tert-butyl (2S)-3-[(2S)-2-methoxycarbonylpyrrolidin-1-yl]-2-methyl-5-oxo-pyrrolidine-1-carboxylate (compound 2b, 1.2 g, crude) in EtOAc (5 mL) was added HCl (20 mL L, 80 mmol, 4 M in dioxane), the reaction mixture was stirred at room temperature for 2 hours. The reaction mixture was concentrated and the residue was purified by prep-HPLC to give compound 2c (186 mg) as a colorless oil. LCMS (M+H$^+$): 227.0.

Step 3: tert-butyl (6S)-3-[(2S)-3-[(2S)-2-methoxycarbonylpyrrolidin-1-yl]-2-methyl-5-oxo-pyrrolidin-1-yl]-6-methyl-6,7-dihydro-4H-pyrazol[1,5-a]pyrazine-5-carboxylate (Compound 2d)

To a solution of tert-butyl (6S)-3-iodo-6-methyl-6,7-dihydro-4H-pyrazolo[1,5-a]pyrazine-5-carboxylate (Intermediate I-1, 482 mg, 1.33 mmol) in dioxane (20 mL) was added methyl (2S)-1-[(2S)-2-methyl-5-oxo-pyrrolidin-3-yl]pyrrolidine-2-carboxylate (349 mg, 1.54 mmol), (1R,2R)—N1,N2-dimethylcyclohexane-1,2-diamine (39 mg, 0.27 mmol), K$_3$PO$_4$ (565 mg, 2.66 mmol) and CuI (52 mg, 0.27 mmol). The reaction mixture was stirred at 110° C. for 12 h under N$_2$ atmosphere and then diluted by EtOAc (50 mL), filtered and the filtrate was concentrated and the residue was purified by prep-HPLC to give compound 2d (0.25 g) as a brown solid. LCMS: (M+H$^+$) 462.2

Step 4: Preparation of methyl (2S)-1-[(2S)-2-methyl-1-[(6S)-6-methyl-5-[(3,4,5-trifluorophenyl)carbamoyl]-6,7-dihydro-4H-pyrazolo[1,5-a]pyrazin-3-yl]-5-oxo-pyrrolidin-3-yl]pyrrolidine-2-carboxylate (Compound 2e)

To a solution of tert-butyl (6S)-3-[(2S)-3-[(2S)-2-methoxycarbonylpyrrolidin-1-yl]-2-methyl-5-oxo-pyrrolidin-1-yl]-6-methyl-6,7-dihydro-4H-pyrazolo[1,5-a]pyrazine-5-carboxylate (compound 2d, 250 mg, 0.54 mmol) in EtOAc (5 mL) was added HCl (10 mL, 40 mmol, 4 M in EtOAc). The reaction mixture was stirred at room temperature for 2 h, and then concentrated to give a brown residue (220 mg). The residue (150 mg) was dissolved in DMF (2 mL), to which were added DIPEA (128 mg, 0.95 mmol) and phenyl N-(3,4,5-trifluorophenyl)carbamate (Intermediate I-3, 113 mg, 0.42 mmol). The reaction mixture was stirred at room temperature for 12 hours, diluted with H$_2$O (20 mL), and extracted 3 times with EtOAc. The combined organic phase was dried and concentrated to give compound 2e (249 mg, crude) as a brown solid. LCMS: (M+H$^+$) 535.2

Step 5: Preparation of (2S)-1-[(2S)-2-methyl-1-[(6S)-6-methyl-5-[(3,4,5-trifluorophenyl)carbamoyl]-6,7-dihydro-4H-pyrazolo[1,5-a]pyrazin-3-yl]-5-oxo-pyrrolidin-3-yl]pyrrolidine-2-carboxylic (Example 2)

To the mixture of methyl (2S)-1-[(2S)-2-methyl-1-[(6S)-6-methyl-5-[(3,4,5-trifluorophenyl)carbamoyl]-6,7-dihydro-4H-pyrazolo[1,5-a]pyrazin-3-yl]-5-oxo-pyrrolidin-3-yl]pyrrolidine-2-carboxylate (compound 2e, 249 mg) in THF/H$_2$O (4 mL, v/v 3/1) was added LiOH.H$_2$O (49 mg, 1.14 mmol), the reaction mixture was stirred at room temperature for 3 hours.

The reaction was acidified to pH=5, concentrated and the residue was purified by prep-HPLC to give Example 2 (77 mg) as a white solid. LCMS (M+H$^+$): 520.9, $^1$H NMR (400 MHz, METHANOL-d$_4$) δ ppm 7.61 (s, 1H), 7.34-7.21 (m, 2H), 5.01 (d, J=16.9 Hz, 1H), 4.97-4.90 (m, 1H), 4.49-4.37 (m, 2H), 4.36-4.28 (m, 3H), 4.22-4.15 (m, 1H), 3.90-3.78 (m, 1H), 3.45-3.30 (m, 1H), 3.06 (dd, J=11.2, 16.1 Hz, 1H), 2.78 (dd, J=7.7, 16.1 Hz, 1H), 2.63-2.50 (m, 1H), 2.31-2.09 (m, 3H), 1.43 (d, J=6.5 Hz, 3H), 1.23 (d, J=6.8 Hz, 3H).

Example 3

2-[Methyl-[1-[(6S)-6-methyl-5-[(3,4,5-trifluorophenyl)carbamoyl]-6,7-dihydro-4H-pyrazolo[1,5-a]pyrazin-3-yl]-5-oxo-pyrrolidin-3-yl]amino]acetic acid

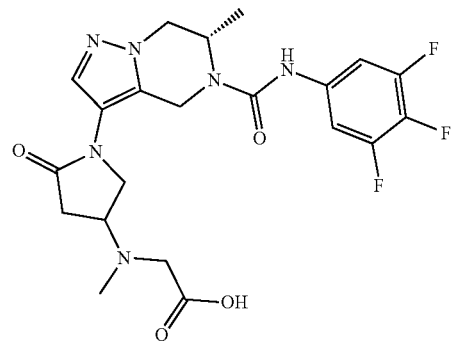 [SMILES: C[C@H]1Cn2ncc(N3CC(N(C)CC(=O)O)CC3=O)c2CN1C(=O)Nc1cc(F)c(F)c(F)c1]

Example 3 was prepared in analogy to Example 1 by using methyl 2-(methylamino)acetate instead of methyl (2S)-pyrrolidine-2-carboxylate. Example 3 (10 mg) was obtained as a white solid. LCMS (M+H$^+$): 480.9, $^1$H NMR (400 MHz, METHANOL-d$_4$) δ ppm 7.70-7.65 (m, 1H), 7.30-7.20 (m, 2H), 5.10-5.01 (m, 1H), 4.95-4.73 (m, 1H), 4.47 (d, J=17.1 Hz, 1H), 4.44-4.34 (m, 1H), 4.32-4.00 (m, 6H), 3.10-2.85 (m, 5H), 1.30-1.15 (m, 3H)

Example 4

(2R)-1-[(2S)-2-methyl-1-[(6S)-6-methyl-5-[(3,4,5-trifluorophenyl)carbamoyl]-6,7-dihydro-4H-pyrazolo[1,5-a]pyrazin-3-yl]-5-oxo-pyrrolidin-3-yl]pyrrolidine-2-carboxylic acid

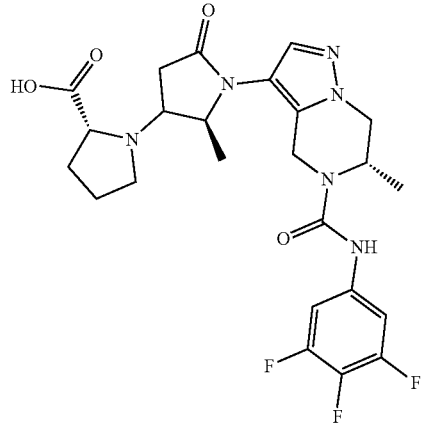 [SMILES: C[C@H]1Cn2ncc(N3C(=O)CC(N4CCC[C@@H]4C(=O)O)[C@@H]3C)c2CN1C(=O)Nc1cc(F)c(F)c(F)c1]

Example 4 was prepared in analogy to Example 2 by using methyl (2R)-pyrrolidine-2-carboxylate instead of methyl (2S)-pyrrolidine-2-carboxylate. Example 4 (38 mg) was obtained as a white solid. LCMS (M+H$^+$): 520.9, $^1$H NMR: (400 MHz, METHANOL-d₄) δ ppm 7.62 (s, 1H), 7.35-7.23 (m, 2H), 5.04 (d, J=17.1 Hz, 1H), 5.00-4.85 (m, 1H), 4.53-4.40 (m, 3H), 4.38-4.27 (m, 2H), 4.23-4.15 (m, 1H), 3.80-3.70 (m, 1H), 3.45-3.35 (m, 1H), 3.07 (dd, J=9.5, 16.4 Hz, 1H), 2.96-2.87 (m, 1H), 2.59-2.47 (m, 1H), 2.45-2.36 (m, 1H), 2.28-2.16 (m, 1H), 2.15-2.03 (m, 1H), 1.37 (d, J=6.3 Hz, 3H), 1.25 (d, J=6.9 Hz, 3H)

Example 5

1-[1-[(6S)-6-methyl-5-[(3,4,5-trifluorophenyl)carbamoyl]-6,7-dihydro-4H-pyrazolo[1,5-a]pyrazin-3-yl]-5-oxo-pyrrolidin-3-yl]pyrrolidine-3-carboxylic acid

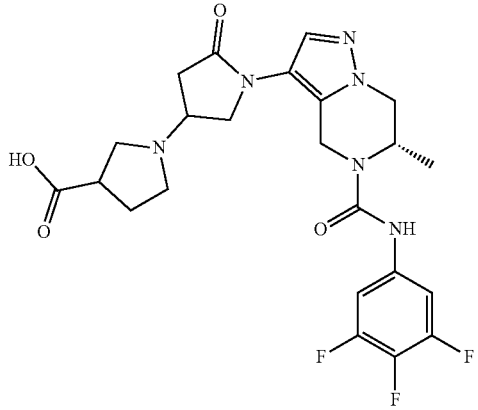 [SMILES: C[C@H]1Cn2ncc(N3CC(N4CCC(C(=O)O)C4)CC3=O)c2CN1C(=O)Nc1cc(F)c(F)c(F)c1]

Example 5 was prepared in analogy to Example 1 by using methyl pyrrolidine-3-carboxylate instead of methyl (2S)-pyrrolidine-2-carboxylate. Example 5 (10 mg) was obtained as a white solid. LCMS (M+H⁺) 506.9, ¹H NMR (400 MHz, DMSO-d₆) δ ppm ¹H NMR (400 MHz, DMSO-d₆) δ=9.19 (s, 1H), 8.30 (br s, 1H), 7.61 (s, 0.5H), 7.60 (s, 0.5H), 7.48-7.38 (m, 2H), 5.03-4.92 (m, 1H), 4.91-4.80 (m, 1H), 4.44-4.32 (m, 1H), 4.24-4.15 (m, 1H), 4.14-4.06 (m, 1H), 3.89-3.83 (m, 2H), 3.50-3.40 (m, 1H), 3.22-3.11 (m, 1H), 2.98-2.86 (m, 1H), 2.86-2.75 (m, 1H), 2.70-2.50 (m, 3H), 2.48-2.32 (m, 1H), 2.05-1.90 (m, 2H), 1.20-1.05 (m, 3H).

Example 6

(2S)-1-[1-[(6S,7S)-6,7-dimethyl-5-[(3,4,5-trifluorophenyl)carbamoyl]-6,7-dihydro-4H-pyrazolo[1,5-a]pyrazin-3-yl]-5-oxo-pyrrolidin-3-yl]pyrrolidine-2-carboxylic acid

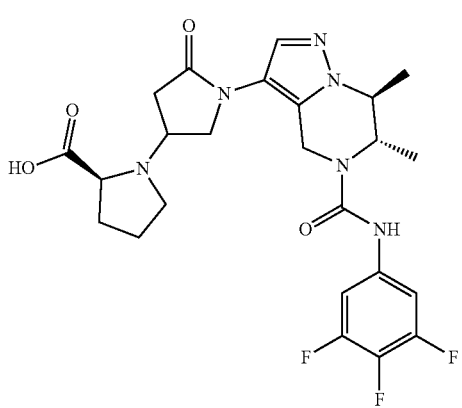 [SMILES: C[C@H]1[C@H](C)n2ncc(N3CC(N4CCC[C@H]4C(=O)O)CC3=O)c2CN1C(=O)Nc1cc(F)c(F)c(F)c1]

The Example 6 was prepared in analogy to Example 1 by using tert-butyl (6S,7S)-3-iodo-6,7-dimethyl-6,7-dihydro-4H-pyrazolo[1,5-a]pyrazine-5-carboxylate (Intermediate I-2) instead of tert-butyl (6S)-3-iodo-6-methyl-6,7-dihydro-4H-pyrazolo[1,5-a]pyrazine-5-carboxylate (Intermediate I-1). Prep-HPLC purification afforded Example 6 as two isomers, Example 6-1 and Example 6-2.

Example 6-1 (14 mg) was obtained as white solid. LCMS (M+H⁺): 521.2, ¹H NMR (400 MHz, METHANOL-d₄) δ ppm 7.64 (s, 1H), 7.55-7.40 (m, 2H), 5.21 (d, J=17.0 Hz, 1H), 4.82 (q, J=6.8 Hz, 1H), 4.52 (d, J=17.0 Hz, 1H), 4.38 (q, J=6.5 Hz, 1H), 4.31-4.15 (m, 2H), 4.03 (dd, J=4.5, 9.7 Hz, 1H), 3.98-3.80 (m, 2H), 3.20 (dt, J=6.6, 10.6 Hz, 1H), 3.14-3.03 (m, 1H), 2.99-2.89 (m, 1H), 2.58-2.41 (m, 1H), 2.34-2.22 (m, 1H), 2.15 (tdd, J=3.2, 6.6, 13.2 Hz, 1H), 2.05-1.94 (m, 1H), 1.43 (d, J=6.6 Hz, 3H), 1.25 (d, J=6.8 Hz, 3H).

Example 6-2 (27 mg) was obtained as white solid. LCMS (M+H⁺): 521.2, ¹H NMR (400 MHz, METHANOL-d₄) δ=7.66 (s, 1H), 7.42-7.30 (m, 2H), 5.08 (d, J=16.9 Hz, 1H), 4.80 (q, J=7.2 Hz, 1H), 4.52 (d, J=16.9 Hz, 1H), 4.43-4.27 (m, 2H), 4.20-4.06 (m, 2H), 3.95 (br dd, J=4.8, 9.8 Hz, 1H), 3.74 (br t, J=7.0 Hz, 1H), 3.24-3.13 (m, 1H), 3.08-2.98 (m, 1H), 2.92-2.83 (m, 1H), 2.54-2.41 (m, 1H), 2.32-2.22 (m, 1H), 2.12 (tdd, J=3.5, 6.6, 9.7 Hz, 1H), 2.00-1.92 (m, 1H), 1.45 (d, J=6.6 Hz, 3H), 1.24 (d, J=7.0 Hz, 3H).

Example 7

2-[1-[(6S)-6-methyl-5-[(3,4,5-trifluorophenyl)carbamoyl]-6,7-dihydro-4H-pyrazolo[1,5-a]pyrazin-3-yl]-5-oxo-pyrrolidin-3-yl]benzoic acid

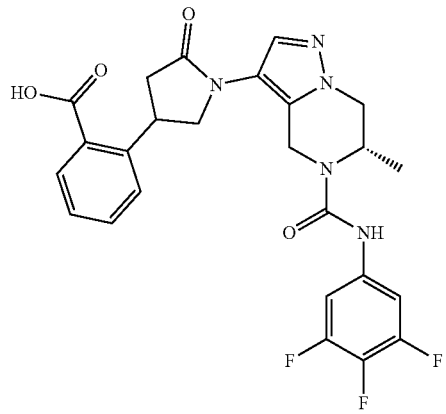 [SMILES: C[C@H]1Cn2ncc(N3CC(c4ccccc4C(=O)O)CC3=O)c2CN1C(=O)Nc1cc(F)c(F)c(F)c1]

The title compound was prepared according to the following scheme:

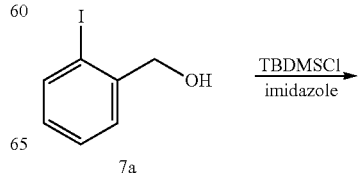

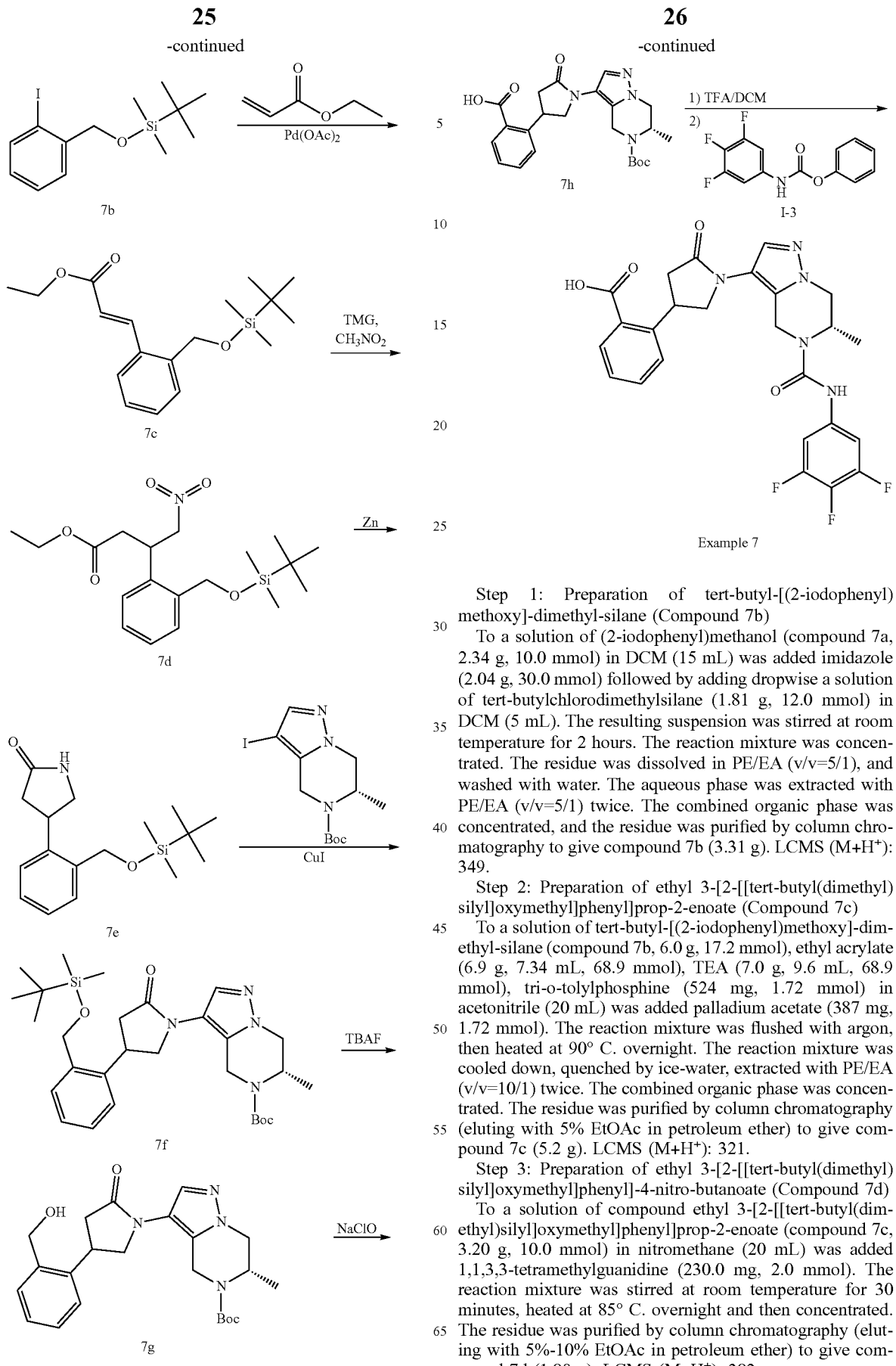

Example 7

Step 1: Preparation of tert-butyl-[(2-iodophenyl)methoxy]-dimethyl-silane (Compound 7b)

To a solution of (2-iodophenyl)methanol (compound 7a, 2.34 g, 10.0 mmol) in DCM (15 mL) was added imidazole (2.04 g, 30.0 mmol) followed by adding dropwise a solution of tert-butylchlorodimethylsilane (1.81 g, 12.0 mmol) in DCM (5 mL). The resulting suspension was stirred at room temperature for 2 hours. The reaction mixture was concentrated. The residue was dissolved in PE/EA (v/v=5/1), and washed with water. The aqueous phase was extracted with PE/EA (v/v=5/1) twice. The combined organic phase was concentrated, and the residue was purified by column chromatography to give compound 7b (3.31 g). LCMS (M+H$^+$): 349.

Step 2: Preparation of ethyl 3-[2-[[tert-butyl(dimethyl)silyl]oxymethyl]phenyl]prop-2-enoate (Compound 7c)

To a solution of tert-butyl-[(2-iodophenyl)methoxy]-dimethyl-silane (compound 7b, 6.0 g, 17.2 mmol), ethyl acrylate (6.9 g, 7.34 mL, 68.9 mmol), TEA (7.0 g, 9.6 mL, 68.9 mmol), tri-o-tolylphosphine (524 mg, 1.72 mmol) in acetonitrile (20 mL) was added palladium acetate (387 mg, 1.72 mmol). The reaction mixture was flushed with argon, then heated at 90° C. overnight. The reaction mixture was cooled down, quenched by ice-water, extracted with PE/EA (v/v=10/1) twice. The combined organic phase was concentrated. The residue was purified by column chromatography (eluting with 5% EtOAc in petroleum ether) to give compound 7c (5.2 g). LCMS (M+H$^+$): 321.

Step 3: Preparation of ethyl 3-[2-[[tert-butyl(dimethyl)silyl]oxymethyl]phenyl]-4-nitro-butanoate (Compound 7d)

To a solution of compound ethyl 3-[2-[[tert-butyl(dimethyl)silyl]oxymethyl]phenyl]prop-2-enoate (compound 7c, 3.20 g, 10.0 mmol) in nitromethane (20 mL) was added 1,1,3,3-tetramethylguanidine (230.0 mg, 2.0 mmol). The reaction mixture was stirred at room temperature for 30 minutes, heated at 85° C. overnight and then concentrated. The residue was purified by column chromatography (eluting with 5%-10% EtOAc in petroleum ether) to give compound 7d (1.80 g). LCMS (M+H$^+$): 382.

Step 4: Preparation of 4-[2-[[tert-butyl(dimethyl)silyl]oxymethyl]phenyl]pyrrolidin-2-one (Compound 7e)

To a solution of ethyl 3-[2-[[tert-butyl(dimethyl)silyl]oxymethyl]phenyl]-4-nitro-butanoate (compound 7d, 1.72 g, 4.5 mmol) in EtOAc (10 mL) and EtOH (10 mL) were added saturated aqueous ammonium chloride solution (10 mL) and zinc (2.35 g, 36.0 mmol). The reaction mixture was heated at 90° C. overnight, and then cooled down and filtrated. The filtrate was concentrated. The residue was treated with water, basified to pH 8.0 with 2.5 M aqueous NaOH solution, and extracted with EtOAc twice. The combined organic phase was dried over $Na_2SO_4$, filtrated and concentrated to give compound 7e (1.37 g, crude), which was used directly in next step. LCMS (M+H$^+$): 306.

Step 5: Preparation of tert-butyl (6S)-3-[4-[2-[[tert-butyl(dimethyl)silyl]oxymethyl]phenyl]-2-oxo-pyrrolidin-1-yl]-6-methyl-6,7-dihydro-4H-pyrazolo[1,5-a]pyrazine-5-carboxylate (Compound 7f)

To a solution of 4-[2-[[tert-butyl(dimethyl)silyl]oxymethyl]phenyl]pyrrolidin-2-one (compound 7e, 1.0 g, 3.30 mmol) in DMSO (15 mL) were added tert-butyl (6S)-3-iodo-6-methyl-6,7-dihydro-4H-pyrazolo[1,5-a]pyrazine-5-carboxylate (Intermediate I-1, 1.2 g, 3.30 mmol), $K_3PO_4$ (1.4 g, 6.60 mmol), (1R,2R)—N1,N2-dimethylcyclohexane-1,2-diamine (188.0 mg, 1.32 mmol) and CuI (126.0 mg, 661 μmol). The reaction mixture was flushed with nitrogen, sealed and heated under microwave at 110° C. for 2 hours. The reaction mixture was cooled down, quenched with ice-water and extracted with EtOAc twice. The combined organic layer was dried over $Na_2SO_4$ and concentrated. The residue was purified by column chromatography to give compound 7f (1.4 g). LCMS (M+H$^+$): 541.

Step 6: Preparation of tert-butyl (6S)-3-[4-[2-(hydroxymethyl)phenyl]-2-oxo-pyrrolidin-1-yl]-6-methyl-6,7-dihydro-4H-pyrazolo[1,5-a]pyrazine-5-carboxylate (Compound 7g)

A mixture of tert-butyl (6S)-3-[4-[2-[[tert-butyl(dimethyl)silyl]oxymethyl]phenyl]-2-oxo-pyrrolidin-1-yl]-6-methyl-6,7-dihydro-4H-pyrazolo[1,5-a]pyrazine-5-carboxylate (compound 7f, 1.41 g, 2.6 mmol) and tetrabutylammonium fluoride solution (1.0 M in THF, 3 mL) was stirred at room temperature for 2 hours. The reaction mixture was concentrated and the residue was purified by column chromatography to give compound 7g (1.1 g). LCMS (M+H$^+$): 427.

Step 7: Preparation of 2-[1-[(6S)-5-tert-butoxycarbonyl-6-methyl-6,7-dihydro-4H-pyrazolo[1,5-a]pyrazin-3-yl]-5-oxo-pyrrolidin-3-yl]benzoic acid (Compound 7h)

To a solution of tert-butyl (6S)-3-[4-[2-(hydroxymethyl)phenyl]-2-oxo-pyrrolidin-1-yl]-6-methyl-6,7-dihydro-4H-pyrazolo[1,5-a]pyrazine-5-carboxylate (compound 7g, 700.0 mg, 1.64 mmol) in acetonitrile (5 mL) and water (10 mL) was added 2,2,6,6-tetramethylpiperidine-N-oxide (25.6 mg, 164 μmol) and potassium bromide (19.5 mg, 164 μmol). After 10 minutes, sodium hypochlorite (14.5%, 2.45 mol/L, 3.35 mL, 8.20 mmol) was added dropwise. Then 2N aqueous sodium hydroxide solution was added to adjust pH=8-10. The reaction mixture was stirred at room temperature for 2 hours, and then at 50° C. for 3 hours. Another batch of NaClO (14.5%, 3.35 mL) was added and the mixture was stirred at 50° C. for another 3 hours, and then quenched with ethanol, concentrated and acidified to pH=4-5, and extracted with EtOAc twice. The organic phase was dried and concentrated to give crude compound 7h (723.0 mg, crude). LCMS (M+H$^+$): 441.

Step 8: Preparation of 2-[1-[(6S)-6-methyl-5-[(3,4,5-trifluorophenyl)carbamoyl]-6,7-dihydro-4H-pyrazolo[1,5-a]pyrazin-3-yl]-5-oxo-pyrrolidin-3-yl]benzoic acid (Example 7)

The mixture of 2-[1-[(6S)-5-tert-butoxycarbonyl-6-methyl-6,7-dihydro-4H-pyrazolo[1,5-a]pyrazin-3-yl]-5-oxo-pyrrolidin-3-yl]benzoic acid (compound 7h, 723.0 mg, 1.64 mmol), 2,2,2-trifluoroacetic acid (5.0 mL) and DCM (2.5 mL) was stirred at room temperature for 30 minutes. The reaction mixture was concentrated, then toluene was added for azeotropic distillation. The residue was dissolved with DCE (10 mL), to which were added DIPEA (2.0 mL) and phenyl N-(3,4,5-trifluorophenyl)carbamate (Intermediate I-3, 658.0 mg, 2.46 mmol). The reaction mixture was heated at 40° C. for 3 hours and then concentrated. The residue was purified by silica gel column chromatography and then prep-HPLC to give Example 7 (460 mg). LCMS (M+H$^+$): 514.2, $^1$H NMR (400 MHz, METHANOL-d$_4$) δ ppm 7.96 (d, J=7.6 Hz, 1H), 7.68-7.55 (m, 3H), 7.43-7.36 (m, 1H), 7.34-7.24 (m, 2H), 5.14-5.04 (m, 1H), 5.00-4.93 (m, 1H), 4.70-4.58 (m, 1H), 4.58-4.50 (m, 1H), 4.34-4.20 (m, 2H), 4.20-4.13 (m, 1H), 3.96-3.87 (m, 1H), 3.02 (dd, J=9.2, 17.2 Hz, 1H), 2.77 (dd, J=7.5, 17.2 Hz, 1H), 1.29 (d, J=7.0 Hz, 3H).

Example 7 could be separated to two isomers, Example 7-1 (peak 1) and Example 7-2 (peak 2), by SFC (chiral column, Chiralcel® OD-H, 5 μm, 20×250 mm; mobile phase, 80% $CO_2$ and 20% MeOH (MeOH+0.5% $NH_3H_2O$); flow rate 65 mL/min, back pressure 100 bar)

Example 7-1, LCMS (M+H$^+$): 514.4, $^1$H NMR (400 MHz, METHANOL-d4) δ ppm 7.85 (d, J=7.3 Hz, 1H), 7.66 (s, 1H), 7.60-7.51 (m, 2H), 7.39-7.34 (m, 1H), 7.34-7.25 (m, 2H), 5.08 (d, J=17.0 Hz, 1H), 5.03-4.95 (m, 1H), 4.65-4.50 (m, 1H), 4.56 (d, J=16.9 Hz, 1H), 4.30 (dd, J=4.4, 12.8 Hz, 1H), 4.26-4.19 (m, 1H), 4.16 (dd, J=1.0, 12.7 Hz, 1H), 3.93 (dd, J=6.7, 9.6 Hz, 1H), 3.01 (dd, J=9.2, 17.2 Hz, 1H), 2.79 (dd, J=7.7, 17.1 Hz, 1H), 1.28 (d, J=6.8 Hz, 3H)

Example 7-2, LCMS (M+H$^+$): 514.4, $^1$H NMR (400 MHz, METHANOL-d4) δ=7.91 (d, J=7.7 Hz, 1H), 7.66 (s, 1H), 7.61-7.53 (m, 2H), 7.41-7.35 (m, 1H), 7.34-7.25 (m, 2H), 5.09 (d, J=16.9 Hz, 1H), 5.00-4.94 (m, 1H), 4.65-4.57 (m, 1H), 4.54 (d, J=17.0 Hz, 1H), 4.36-4.23 (m, 2H), 4.19-4.13 (m, 1H), 3.90 (dd, J=6.4, 9.6 Hz, 1H), 3.02 (dd, J=9.2, 17.1 Hz, 1H), 2.79 (dd, J=7.5, 17.1 Hz, 1H), 1.28 (d, J=6.8 Hz, 3H).

Example 8

3-[1-[(6S)-6-methyl-5-[(3,4,5-trifluorophenyl)carbamoyl]-6,7-dihydro-4H-pyrazolo[1,5-a]pyrazin-3-yl]-5-oxo-pyrrolidin-3-yl]benzoic acid

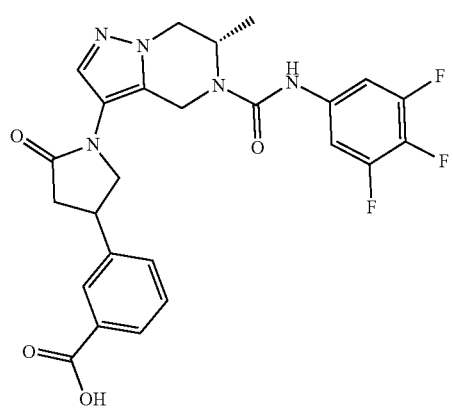 [SMILES: C[C@H]1Cn2ncc(N3CC(c4cccc(C(=O)O)c4)CC3=O)c2CN1C(=O)Nc1cc(F)c(F)c(F)c1]

The title compound was prepared according to the following scheme:

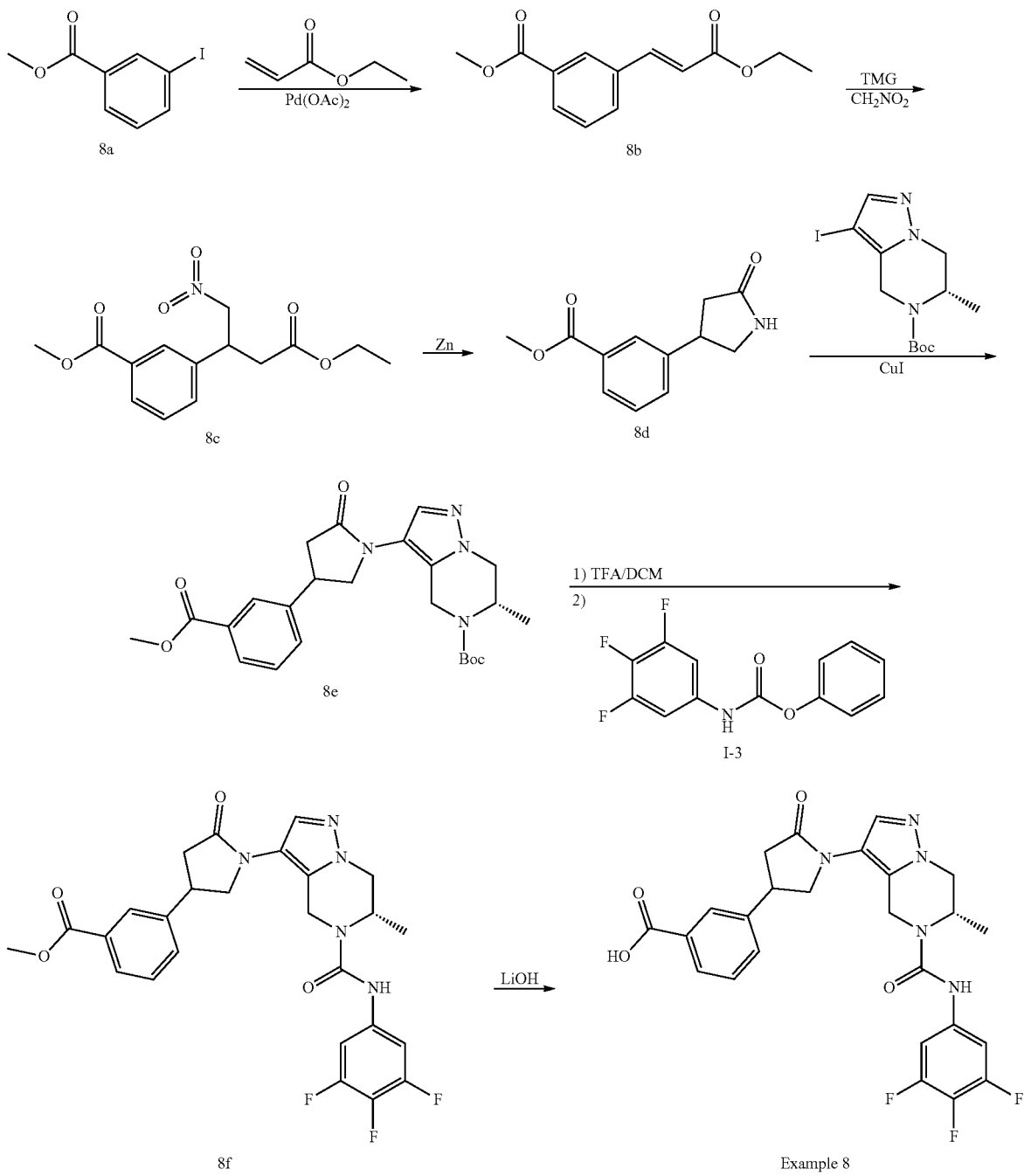

Preparation of tert-butyl (6S)-3-[4-(3-methoxycarbonylphenyl)-2-oxo-pyrrolidin-1-yl]-6-methyl-6,7-dihydro-4H-pyrazolo[1,5-a]pyrazine-5-carboxylate (Compound 8e)

Compound 8e was prepared in analogy to compound 7f by using methyl 3-iodobenzoate (compound 8a) instead of tert-butyl-[(2-iodophenyl)methoxy]-dimethyl-silane (compound 7b). Compound 8e was obtained as a solid (263 mg). LCMS (M+H$^+$): 455.

Preparation of methyl 3-[1-[(6S)-6-methyl-5-[(3,4,5-trifluorophenyl)carbamoyl]-6,7-dihydro-4H-pyrazolo[1,5-a]pyrazin-3-yl]-5-oxo-pyrrolidin-3-yl]benzoate (Compound 8f)

A mixture of tert-butyl (6S)-3-[4-(3-methoxycarbonylphenyl)-2-oxo-pyrrolidin-1-yl]-6-methyl-6,7-dihydro-4H-pyrazolo[1,5-a]pyrazine-5-carboxylate (compound 8e, 260.0 mg, 572 mol), 2,2,2-trifluoroacetic acid (2 mL) and DCM (1 mL) was stirred at room temperature for 30 minutes. The reaction mixture was concentrated, then toluene was added for azeotropic distillation. The residue was dissolved in DCM (3 mL), to which were then added DIPEA (1.0 mL) and phenyl N-(3,4,5-trifluorophenyl)carbamate (Intermediate I-3, 229 mg, 858 μmol). The reaction mixture was heated at 40° C. for 3 hours and then concentrated. The residue was purified by column chromatography (eluting with 50%-60% EtOAc (containing 10% MeOH) in petroleum ether) to afford compound 8f (287 mg). LCMS (M+H$^+$): 528.

Preparation of 3-[1-[(6S)-6-methyl-5-[(3,4,5-trifluorophenyl)carbamoyl]-6,7-dihydro-4H-pyrazolo[1,5-a]pyrazin-3-yl]-5-oxo-pyrrolidin-3-yl]benzoic acid (Example 8)

To a solution of methyl 3-[1-[(6S)-6-methyl-5-[(3,4,5-trifluorophenyl)carbamoyl]-6,7-dihydro-4H-pyrazolo[1,5-a]pyrazin-3-yl]-5-oxo-pyrrolidin-3-yl]benzoate (compound 8f, 260 mg, 493 μmol) in THF (1.3 mL) was added lithium hydroxide aqueous solution (2 M, 1.3 mL, 2.6 mmol). The reaction mixture was stirred at room temperature for 2 hours, acidified to pH=4-5, and concentrated. The residue was purified by prep-HPLC to give Example 8 (120 mg). LCMS (M+H$^+$): 514. $^1$H NMR (400 MHz, METHANOL-d$_4$) δ=8.11-8.04 (m, 1H), 8.00-7.94 (m, 1H), 7.72-7.63 (m, 2H), 7.55-7.49 (m, 1H), 7.33-7.25 (m, 2H), 5.16-5.06 (m, 1H), 5.03-4.94 (m, 1H), 4.63-4.52 (m, 1H), 4.35-4.15 (m, 3H), 3.99-3.89 (m, 2H), 3.08-2.98 (m, 1H), 2.82-2.71 (m, 1H), 1.33-1.24 (m, 3H).

Example 9

(2R)-1-[1-[(6S)-6-methyl-5-[(3,4,5-trifluorophenyl)carbamoyl]-6,7-dihydro-4H-pyrazolo[1,5-a]pyrazin-3-yl]-5-oxo-pyrrolidin-3-yl]pyrrolidine-2-carboxylic acid

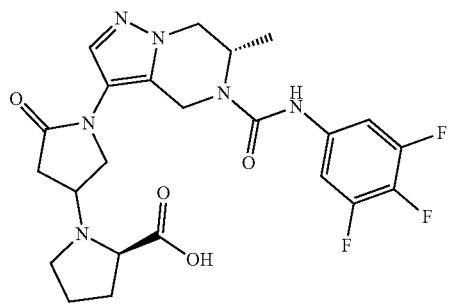 [SMILES: C[C@H]1Cn2ncc(N3CC(N4CCC[C@@H]4C(=O)O)CC3=O)c2CN1C(=O)Nc1cc(F)c(F)c(F)c1]

Example 9 was prepared in analogy to Example 1 by using methyl (2R)-pyrrolidine-2-carboxylate instead of methyl (2S)-pyrrolidine-2-carboxylate. Example 9 (54 mg) was obtained as a white solid. LCMS (M+H+) 507.3, $^1$H NMR (400 MHz, METHANOL-d4) δ ppm 7.71-7.62 (m, 1H), 7.39-7.25 (m, 2H), 5.13-5.02 (m, 1H), 5.00-4.85 (m, 1H), 4.53-3.98 (m, 7H), 3.88-3.76 (m, 1H), 3.39-3.34 (m, 1H), 3.14-3.05 (m, 1H), 2.98-2.85 (m, 1H), 2.65-2.49 (m, 1H), 2.40-2.27 (m, 1H), 2.26-2.15 (m, 1H), 2.11-1.93 (m, 1H), 1.30-1.20 (m, 3H)

Example 10

3-Fluoro-2-[1-[(6S)-6-methyl-5-[(3,4,5-trifluorophenyl)carbamoyl]-6,7-dihydro-4H-pyrazolo[1,5-a]pyrazin-3-yl]-5-oxo-pyrrolidin-3-yl]benzoic acid

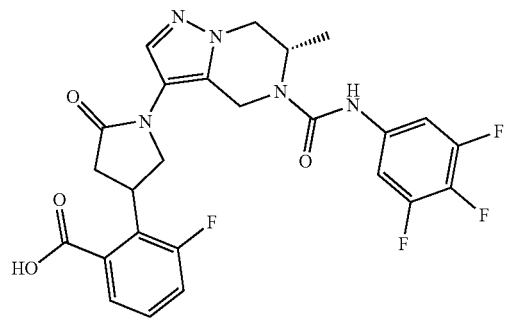 [SMILES: C[C@H]1Cn2ncc(N3CC(c4c(F)cccc4C(=O)O)CC3=O)c2CN1C(=O)Nc1cc(F)c(F)c(F)c1]

Example 10 was prepared in analogy to Example 7 by using (2-bromo-3-fluoro-phenyl)methanol instead of (2-iodophenyl)methanol. Separation of the final product by SFC gave Example 10 as two isomers, Example 10-1 and Example 10-2. SFC conditions: chiral column, chiralcel® OZ-H, 5 μm, 20×250 mm; mobile phase, 80% CO$_2$ and 20% MeOH (MeOH+0.5% NH$_3$H$_2$O); flow rate, 65 mL/min, back pressure 100 bar.

Example 10-1 was obtained (12 mg) as a white solid. LCMS (M+H)$^+$: 532.2, $^1$H NMR (400 MHz, METHANOL-d$_4$) δ ppm 7.55 (s, 1H), 7.39 (d, J=7.0 Hz, 1H), 7.29-7.06 (m, 4H), 4.97 (d, J=16.9 Hz, 1H), 4.93-4.84 (m, 1H), 4.49-4.42 (m, 2H), 4.24-4.14 (m, 1H), 4.10-4.00 (m, 2H), 3.97-3.86 (m, 1H), 2.88-2.72 (m, 2H), 1.17 (d, J=6.8 Hz, 3H).

Example 10-2 was obtained (8 mg) as a white solid. LCMS (M+H)$^+$: 532.2, $^1$H NMR (400 MHz, METHANOL-d$_4$) δ ppm 7.67 (s, 1H), 7.57 (d, J=7.6 Hz, 1H), 7.45-7.20 (m, 4H), 5.14 (d, J=17.1 Hz, 1H), 5.03-4.95 (m, 1H), 4.64 (br d, J=8.2 Hz, 1H), 4.55 (d, J=17.0 Hz, 1H), 4.31 (dd, J=4.5, 12.5 Hz, 1H), 4.25-4.13 (m, 2H), 4.03-3.96 (m, 1H), 3.01-2.85 (m, 2H), 1.29 (d, J=7.0 Hz, 3H).

Example 11

2-Fluoro-6-[1-[(6S)-6-methyl-5-[(3,4,5-trifluorophenyl)carbamoyl]-6,7-dihydro-4H-pyrazolo[1,5-a]pyrazin-3-yl]-5-oxo-pyrrolidin-3-yl]benzoic acid

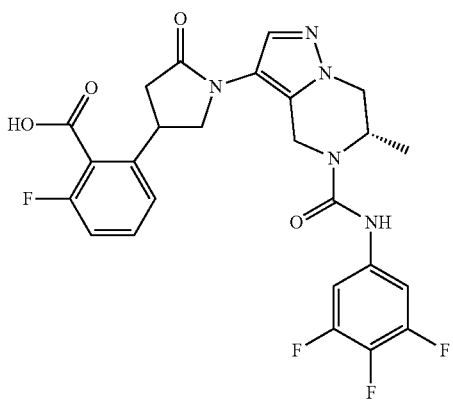 [SMILES: C[C@H]1Cn2ncc(N3CC(c4cccc(F)c4C(=O)O)CC3=O)c2CN1C(=O)Nc1cc(F)c(F)c(F)c1]

Example 11 was prepared in analogy to Example 7 by using (2-bromo-6-fluoro-phenyl)methanol instead of (2-iodophenyl)methanol. Separation of the final product by SFC gave Example 11 as two isomers, Example 11-1 and Example 11-2. SFC conditions: chiral column, Chiralcel® OZ-H, 5 μm, 20×250 mm; mobile phase, 80% CO$_2$ and 20% MeOH (MeOH+0.5% NH$_3$H$_2$O); flow rate, 65 mL/min, back pressure 100 bar.

Example 11-1 was obtained (22 mg) as a white solid. LCMS (M+H)$^+$: 532.2, $^1$H NMR (400 MHz, METHANOL-d$_4$) δ ppm 7.55 (s, 1H), 7.39-7.29 (m, 1H), 7.26-7.14 (m, 3H), 6.97 (t, J=8.7 Hz, 1H), 4.95 (d, J=16.9 Hz, 1H), 4.91-4.83 (m, 1H), 4.46 (d, J=16.9 Hz, 1H), 4.26-4.14 (m, 1H), 4.12-4.01 (m, 2H), 3.99-3.81 (m, 2H), 2.93-2.80 (m, 1H), 2.76-2.65 (m, 1H), 1.16 (d, J=6.8 Hz, 3H).

Example 11-2 was obtained (22 mg) as a white solid. LCMS (M+H)$^+$: 532.2, $^1$H NMR (400 MHz, METHANOL-d$_4$) δ ppm 7.66 (s, 1H), 7.47-7.26 (m, 4H), 7.08 (t, J=8.4 Hz, 1H), 5.16 (d, J=16.9 Hz, 1H), 5.05-4.96 (m, 1H), 4.53 (d, J=16.9 Hz, 1H), 4.34-4.12 (m, 3H), 4.11-3.90 (m, 2H), 3.04-2.93 (m, 1H), 2.93-2.81 (m, 1H), 1.28 (d, J=6.8 Hz, 3H).

Example 12

2-[[1-[(6S)-6-methyl-5-[(3,4,5-trifluorophenyl)carbamoyl]-6,7-dihydro-4H-pyrazolo[1,5-a]pyrazin-3-yl]-5-oxo-pyrrolidin-3-yl]amino]benzoic acid

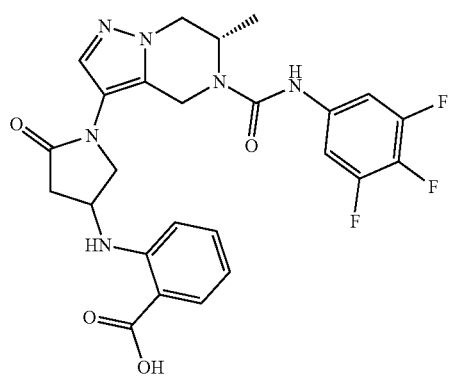 [SMILES: C[C@H]1Cn2ncc(N3CC(Nc4ccccc4C(=O)O)CC3=O)c2CN1C(=O)Nc1cc(F)c(F)c(F)c1]

The title compound was prepared according to the following scheme:

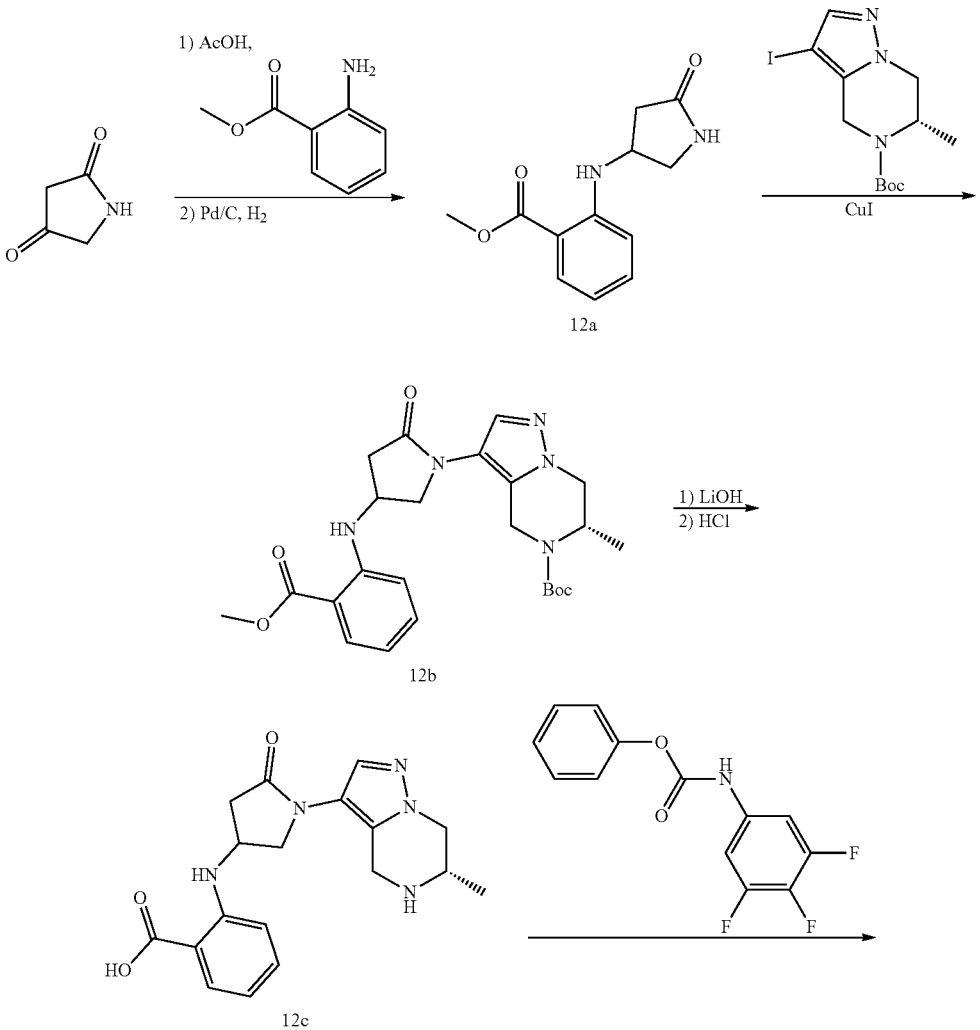

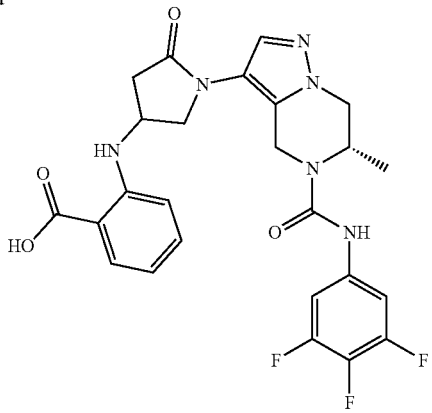

Example 12

Step 1: Preparation of methyl 2-[(5-oxopyrrolidin-3-yl)amino]benzoate (Compound 12a)

A mixture of pyrrolidine-2,4-dione (300 mg, 3.03 mmol) and methyl 2-aminobenzoate (0.43 mL, 3.33 mmol), AcOH (182 mg, 3.03 mmol) in DCE (10 mL) was stirred at 50° C. for 16 hours. The reaction mixture was concentrated to give a yellow solid. The solid was dissolved in methanol (10 mL), to which were added Pd/C (69 mg, 0.3 mmol). The resulting mixture was stirred under $H_2$ (50 psi) for 16 hours at room temperature, and then filtered. The filtrate was concentrated, and the residue was purified by prep-TLC (PE: EtOAc=1:1) to give compound 12a (170 mg) as a colorless oil. LCMS (M+H$^+$) 235.0

Step 2: Preparation of tert-butyl (6S)-3-[4-(2-methoxycarbonylanilino)-2-oxo-pyrrolidin-1-yl]-6-methyl-6,7-dihydro-4H-pyrazolo[1,5-a]pyrazine-5-carboxylate (Compound 12b)

A mixture of methyl 2-[(5-oxopyrrolidin-3-yl)amino]benzoate (compound 12a, 170 mg, 0.73 mmol), tert-butyl (6S)-3-iodo-6-methyl-6,7-dihydro-4H-pyrazolo[1,5-a]pyrazine-5-carboxylate (Intermediate I-1, 290 mg, 0.8 mmol), (1R, 2R)—N1,N2-dimethylcyclohexane-1,2-diamine (21 mg, 0.15 mmol), CuI (28 mg, 0.15 mmol) and $K_3PO_4$ (308 mg) in 1,4-dioxane (15 mL) was stirred at 110° C. under $N_2$ for 32 hours. The reaction mixture was filtered, and the filtrate was concentrated. The residue was purified by prep-TLC (PE: EtOAc, v/v=1/3) to give compound 12b (30 mg) as a yellow oil. LCMS (M+H$^+$) 470.2

Step 3: Preparation of 2-[[1-[(6S)-6-methyl-4,5,6,7-tetrahydropyrazolo[1,5-a]pyrazin-3-yl]-5-oxo-pyrrolidin-3-yl]amino]benzoic acid (Compound 12c)

To a solution of tert-butyl (6S)-3-[4-(2-methoxycarbonylanilino)-2-oxo-pyrrolidin-1-yl]-6-methyl-6,7-dihydro-4H-pyrazolo[1,5-a]pyrazine-5-carboxylate (compound 12b, 30 mg) in THF (2 mL), methanol (2 mL) and water (2 mL) was added LiOH (6 mg). The reaction mixture was stirred at room temperature for 2 hours and then concentrated. The obtained residue was dissolved in EtOAc (2 mL), to which was added a solution of HCl in EtOAc (4 M, 0.08 mL).

The reaction mixture was stirred at room temperature for 2 hours, and concentrated to give crude compound 12c (21 mg) as a white solid. LCMS (M+H$^+$) 356.1

Step 4: Preparation of 2-[[1-[(6S)-6-methyl-5-[(3,4,5-trifluorophenyl)carbamoyl]-6,7-dihydro-4H-pyrazolo[1,5-a]pyrazin-3-yl]-5-oxo-pyrrolidin-3-yl]amino]benzoic acid (Example 12)

A mixture of 2-[[1-[(6S)-6-methyl-4,5,6,7-tetrahydropyrazolo[1,5-a]pyrazin-3-yl]-5-oxo-pyrrolidin-3-yl]amino] benzoic acid (compound 12c, 21 mg) and phenyl N-(3,4,5-trifluorophenyl)carbamate (18 mg) and triethylamine (0.02 mL) in DCM (3 mL) was stirred at room temperature for 3 hours. The reaction mixture was concentrated, and the residue was purified by prep-HPLC to give Example 12 as a yellow oil. LCMS (M+H$^+$) 529.1, $^1$H NMR (400 MHz, DMSO-d$_6$) δ ppm 7.90-7.80 (m, 1H), 7.80-7.65 (m, 1H), 7.60-7.50 (m, 1H), 7.35-7.20 (m, 1H), 6.80-6.70 (m, 1H), 6.65-6.52 (m, 1H), 5.25-5.00 (m, 1H), 4.95-4.85 (m, 1H), 4.49-4.29 (m, 2H), 4.28-4.01 (m, 3H), 3.70-3.50 (m, 1H), 3.07-2.87 (m, 1H), 2.39-2.23 (m, 1H), 1.20-1.10 (m, 3H)

Example 13

2-[7-[(6S)-6-methyl-5-[(3,4,5-trifluorophenyl)carbamoyl]-6,7-dihydro-4H-pyrazolo[1,5-a]pyrazin-3-yl]-6-oxo-3-oxa-7,9-diazabicyclo[3.3.1]nonan-9-yl]acetic acid

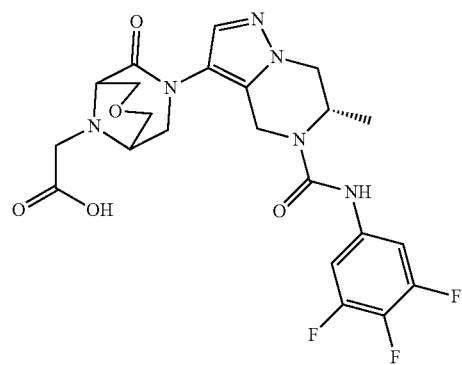 [SMILES: C[C@H]1Cn2ncc(N3CC4COCC(C3=O)N4CC(=O)O)c2CN1C(=O)Nc1cc(F)c(F)c(F)c1]

The title compound was prepared according to the following scheme:

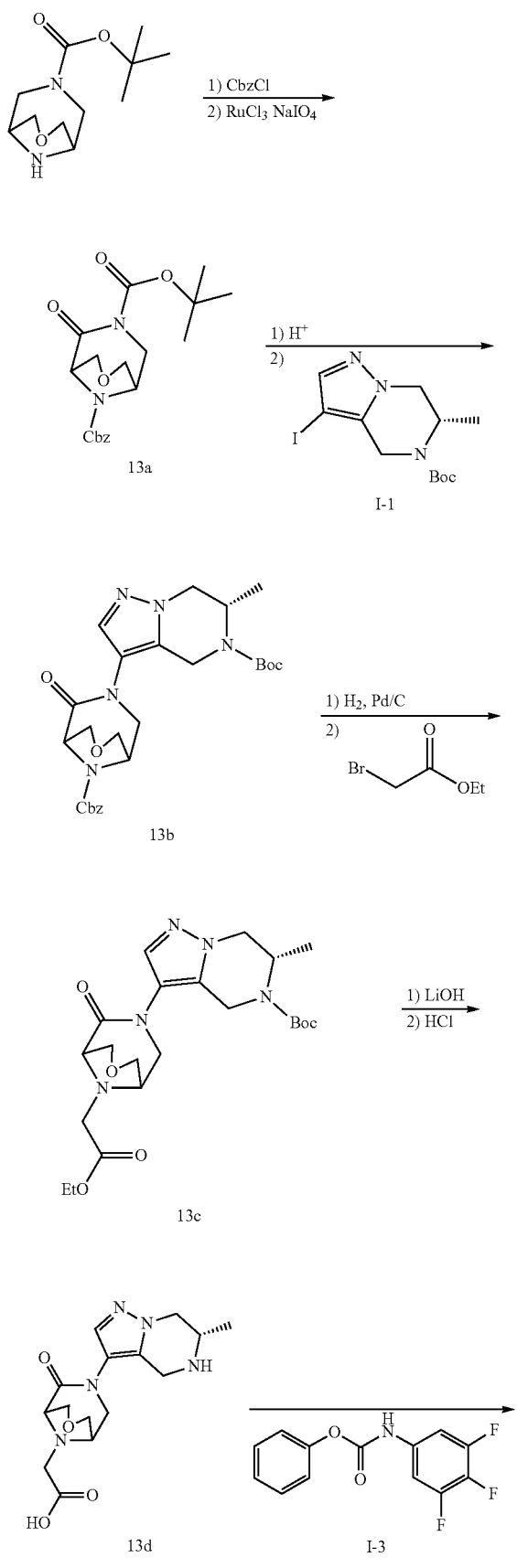

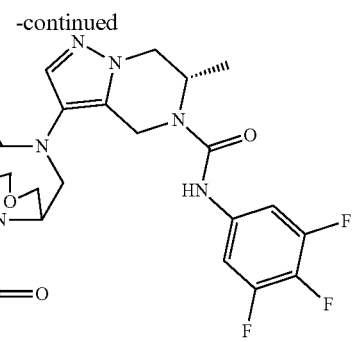

Example 13

Preparation of O9-benzyl O7-tert-butyl 6-oxo-3-oxa-7,9-diazabicyclo[3.3.1]nonane-7,9-dicarboxylate (Compound 13a)

To a solution tert-butyl 3-oxa-7,9-diazabicyclo[3.3.1]nonane-7-carboxylate (400 mg, 1.75 mmol) and Et$_3$N (0.49 mL, 3.5 mmol) in DCM (10 mL) was added CbzCl (448 mg, 2.63 mmol) at room temperature. The reaction mixture was stirred at room temperature for 2 hours and then water (10.0 mL) was added, and the mixture is extracted three times with EtOAc (30 mL each).

The combined organic phase was dried over Na$_2$SO$_4$ and concentrated. The residue was purified by silica gel column chromatography (PE: EtOAc, from 10:1 to 2:1) to give a white solid (300 mg). The solid was dissolved in ACN (8 mL) and water (2 mL), to which were added RuCl$_3$ (35 mg, 0.170 mmol) and NaIO$_4$ (532 mg, 2.48 mmol). The reaction mixture was stirred at room temperature for 36 hours and water (10 mL) was added, and the mixture was extracted three times with EtOAc (20 mL). The combined organic phase was dried over Na$_2$SO$_4$ and concentrated. The residue was purified by column (PE: EtOAc, from 10:1 to 1:1) to give the desired product 13a as a yellow oil (150 mg). LCMS (M-100+H$^+$) 277.1

Preparation of benzyl 7-[(6S)-5-tert-butoxycarbonyl-6-methyl-6,7-dihydro-4H-pyrazolo[1,5-a]pyrazin-3-yl]-6-oxo-3-oxa-7,9-diazabicyclo[3.3.1]nonane-9-carboxylate (Compound 13b)

To a solution of O9-benzyl O7-tert-butyl 6-oxo-3-oxa-7,9-diazabicyclo[3.3.1]nonane-7,9-dicarboxylate (compound 13a, 150 mg, 0.400 mmol) in EtOAc (5 mL) was added a solution of HCl in EtOAc (4 M, 10 mL). The mixture was stirred at room temperature for 2 hours, and concentrated. The crude material was dissolved in 1,4-dioxane (10 mL), to which were tert-butyl (6S)-3-iodo-6-methyl-6,7-dihydro-4H-pyrazolo[1,5-a]pyrazine-5-carboxylate (Intermediate I-1, 158 mg, 0.430 mmol) and K$_3$PO$_4$ (154 mg, 0.720 mmol), CuI (14 mg, 0.070 mmol), (1R,2R)—N1,N2-dimethylcyclohexane-1,2-diamine (11 mg, 0.070 mmol) under N$_2$. The resulting mixture was stirred at room temperature for 14 hours. After cooled down, the reaction mixture was filtered, and concentrated under the reduced pressure. The residue was purified by silica gel column chromatography (PE: EtOAc from 10:1 to 1:1) to give the compound 13b (80 mg) as a yellow oil. LCMS (M+H$^+$) 512.2

Preparation of tert-butyl (6S)-3-[9-(2-ethoxy-2-oxo-ethyl)-6-oxo-3-oxa-7,9-diazabicyclo[3.3.1]nonan-7-yl]-6-methyl-6,7-dihydro-4H-pyrazolo[1,5-a]pyrazine-5-carboxylate (Compound 13c)

A mixture of benzyl 7-[(6S)-5-tert-butoxycarbonyl-6-methyl-6,7-dihydro-4H-pyrazolo[1,5-a]pyrazin-3-yl]-6-oxo-3-oxa-7,9-diazabicyclo[3.3.1]nonane-9-carboxylate (compound 13b, 40 mg, 0.080 mmol) and Pd/C (2 mg, 0.020 mmol) in MeOH (5 mL) was stirred under $H_2$ at room temperature for 14 hours. The reaction mixture was filtered and concentrated. The residue was purified by prep-TLC (DCM: MeOH=10:1) to give tert-butyl (6S)-6-methyl-3-(6-oxo-3-oxa-7,9-diazabicyclo[3.3.1]nonan-7-yl)-6,7-dihydro-4H-pyrazolo[1,5-a]pyrazine-5-carboxylate as a colorless oil (18 mg). This compound was dissolved in ACN (10 mL), to which were added $K_2CO_3$ (14 mg, 0.10 mmol) and ethyl 2-bromoacetate (0.01 mL, 0.070 mmol, 1.5 eq). The reaction mixture was stirred at room temperature for 14 hours, and then concentrated to give crude compound 13c as a yellow oil (18 mg). LCMS (M+H$^+$) 464.1

Preparation of 2-[7-[(6S)-6-methyl-4,5,6,7-tetrahydropyrazolo[1,5-a]pyrazin-3-yl]-6-oxo-3-oxa-7,9-diazabicyclo[3.3.1]nonan-9-yl]acetic acid (Compound 13d)

To a mixture of tert-butyl (6S)-3-[9-(2-ethoxy-2-oxo-ethyl)-6-oxo-3-oxa-7,9-diazabicyclo[3.3.1]nonan-7-yl]-6-methyl-6,7-dihydro-4H-pyrazolo[1,5-a]pyrazine-5-carboxylate (compound 13c, 18 mg, 0.04 mmol) of water (1 mL), methanol (1 mL) and THF (1 mL) was added LiOH (4 mg, 0.08 mmol) at room temperature. The reaction mixture was stirred at room temperature for 2 hours, and then concentrated. The residue was purified by prep-TLC (DCM: MeOH=10:1) to 2-[7-[(6S)-5-tert-butoxycarbonyl-6-methyl-6,7-dihydro-4H-pyrazolo[1,5-a]pyrazin-3-yl]-6-oxo-3-oxa-7,9-diazabicyclo[3.3.1]nonan-9-yl]acetic acid as a yellow oil (12 mg). This acid was dissolved in EtOAc (5 mL), to which was added a solution of HCl in EtOAc (10 mL, 0.03 mmol). The reaction mixture was stirred at room temperature for 2 hours, and concentrated to give crude compound 13d (11 mg) as a yellow oil.

Preparation of 2-[7-[(6S)-6-methyl-5-[(3,4,5-trifluorophenyl)carbamoyl]-6,7-dihydro-4H-pyrazolo[1,5-a]pyrazin-3-yl]-6-oxo-3-oxa-7,9-diazabicyclo[3.3.1]nonan-9-yl]acetic acid (Example 13)

To a mixture of 2-[7-[(6S)-6-methyl-4,5,6,7-tetrahydropyrazolo[1,5-a]pyrazin-3-yl]-6-oxo-3-oxa-7,9-diazabicyclo[3.3.1]nonan-9-yl]acetic acid (compound 13d, 11 mg, 0.03 mmol) and DIPEA (0.01 mL, 0.070 mmol) in DMF (2 mL) was added phenyl N-(3,4,5-trifluorophenyl)carbamate (Intermediate I-3, 11 mg, 0.04 mmol). The reaction mixture was stirred at room temperature for 16 hours, and then concentrated. The residue was purified by HPLC to give Example 13 (3.5 mg) as a white solid. LCMS (M+H$^+$) 509.1; $^1$H NMR (400 MHz, DMSO-d6) δ ppm 9.30-9.20 (m, 1H), 7.66 (s, 0.5H), 7.65 (s, 0.5H), 7.50-7.38 (m, 1H), 4.91-4.73 (m, 2H), 4.43 (s, 1H), 4.32 (m, 1H), 4.27-4.12 (m, 3H), 4.07-3.85 (m, 3H), 3.78-3.62 (m, 5H), 1.20-1.10 (m, 3H)

Example 14

4-Fluoro-2-[1-[(6S)-6-methyl-5-[(3,4,5-trifluorophenyl)carbamoyl]-6,7-dihydro-4H-pyrazolo[1,5-a]pyrazin-3-yl]-5-oxo-pyrrolidin-3-yl]benzoic acid

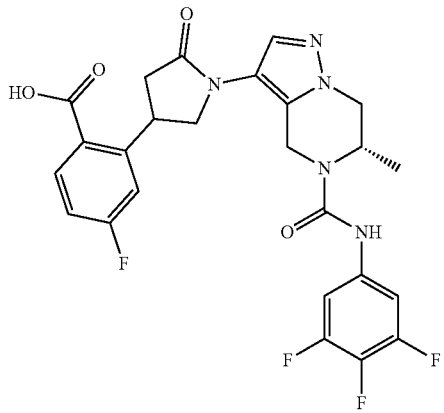

The title compound was prepared according to the following scheme:

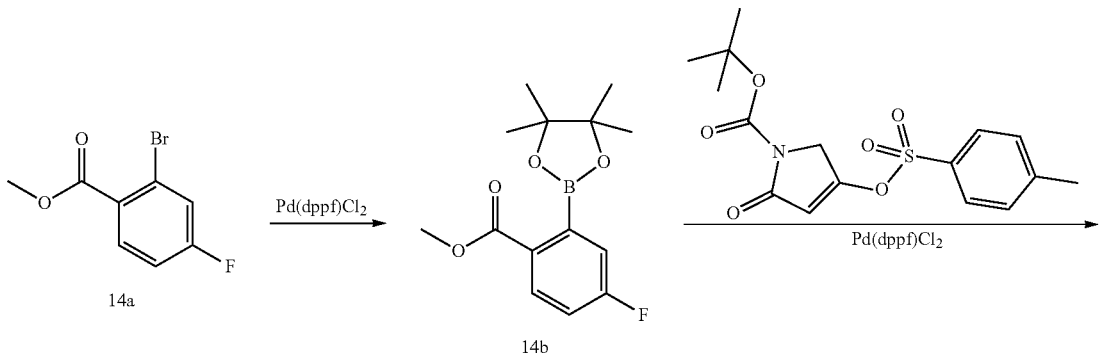

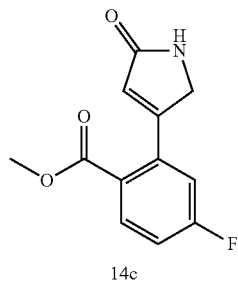
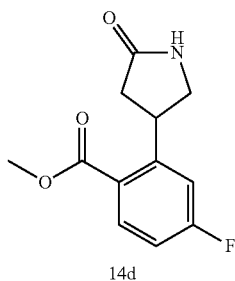
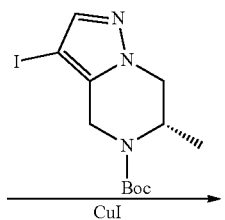

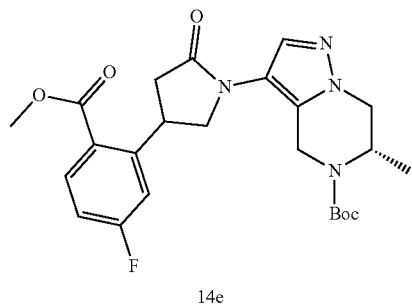
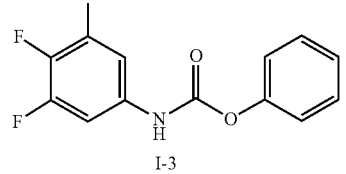

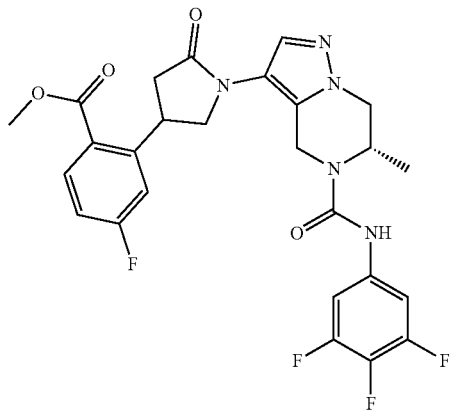
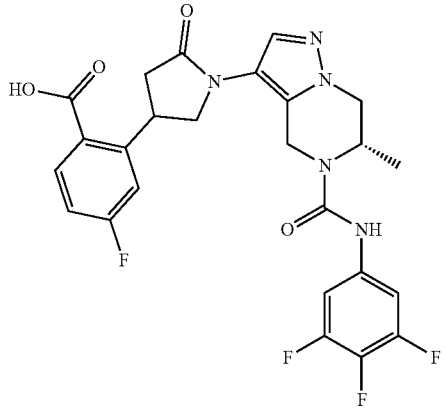 [SMILES: C[C@H]1Cn2ncc(N3CC(c4cc(F)ccc4C(=O)O)CC3=O)c2CN1C(=O)Nc1cc(F)c(F)c(F)c1]

Step 1: Preparation of methyl 4-fluoro-2-(4,4,5,5-tetramethyl-1,3,2-dioxaborolan-2-yl)benzoate (Compound 14b)

A mixture of methyl 2-bromo-4-fluorobenzoate (compound 14a, 1 g, 4.29 mmol), 4,4,4',4',5,5,5',5'-octamethyl-2,2'-bi(1,3,2-dioxaborolane) (1.63 g, 6.44 mmol), PdCl$_2$(DPPF) (350 mg, 429 μmol) and potassium acetate (632 mg, 6.44 mmol) in dioxane (30 mL) was heated to 90° C. and stirred for 2 hours under nitrogen. The crude reaction mixture was concentrated in vacuo. The residue was purified by flash chromatography (silica gel, 40 g, 0% to 10% EtOAc in petroleum ether) to give compound 14b as colorless oil (1 g), LCMS (M+H$^+$): 281.

Step 2: Preparation of methyl 4-fluoro-2-(5-oxo-tetramethyl-1,3,2-dihydropyrrol-3-yl)benzoate (Compound 14c)

A mixture of methyl 4-fluoro-2-(4,4,5,5-tetramethyl-1-fluoro-1,3,2-dioxaborolan-2-yl)benzoate (compound 14b, 951 mg, 3.4 mmol), tert-butyl 2-oxo-4-(tosyloxy)-2,5-dihydro-1H-pyrrole-1-carboxylate (0.8 g, 2.26 mmol, see J. Org. Chem. 2002, 67, 4702 for its synthesis), PdCl$_2$(DPPF) (162 mg, 226 μmol) and K$_2$CO$_3$ (626 mg, 4.53 mmol) in dioxane/H$_2$O(10:1) (20 mL) was heated to 90° C. and stirred for 2 hours under nitrogen. The reaction mixture was filtered through celite. The filtrate was concentrated in vacuo. The residue was purified by flash chromatography (silica gel, 40 g, 0% to 100% EtOAc in petroleum ether, EtOAc contain 10% MeOH) to give compound 14c (150 mg) as light yellow oil. LCMS (M+H$^+$): 236.

Step 3: Preparation of methyl 4-fluoro-2-(5-oxopyrrolidin-3-yl)benzoate (Compound 14d)

A mixture of methyl 4-fluoro-2-(5-oxo-2,5-dihydro-1H-pyrrol-3-yl)benzoate (compound 14c, 100 mg, 425 μmol) and Pd—C (50 mg) in MeOH (20 mL) was heated to 55° C.

and stirred for 20 hours under hydrogen balloon. The reaction mixture was filtered through celite and the filtrate was concentrated to give compound 14d as white solid (40 mg). LCMS (M+H$^+$): 238.

Step 4: Preparation of tert-butyl (6S)-3-[4-(5-fluoro-2-methoxycarbonyl-phenyl)-2-oxo-pyrrolidin-1-yl]-6-methyl-6,7-dihydro-4H-pyrazolo[1,5-a]pyrazine-5-carboxylate (Compound 14e)

To a 10 mL microwave vial was added (S)-tert-butyl 3-iodo-6-methyl-6,7-dihydropyrazolo[1,5-a]pyrazine-5(4H)-carboxylate (intermediate I-1, 100 mg, 275 μmol), (1R,2R)—N1,N2-dimethylcyclohexane-1,2-diamine (15.7 mg, 110 μmol), methyl 4-fluoro-2-(5-oxopyrrolidin-3-yl)benzoate (compound 14d, 40 mg, 169 μmol), copper (I) iodide (10.5 mg, 55.1 μmol) and potassium phosphate (117 mg, 551 μmol) in DMSO (5 mL). The vial was capped and the reaction mixture was heated in the microwave at 120° C. and stirred for 4 hours. After cooled down to room temperature, the reaction mixture was poured into 20 mL of EtOAc and washed with H$_2$O (20 mL) and brine (20 mL). The organic layer was dried over Na$_2$SO$_4$ and concentrated in vacuo. The crude product was purified by flash chromatography (silica gel, 12 g, 0% to 100% EtOAc in petroleum ether, EtOAc contain 10% MeOH) to give compound 14e as light yellow oil (40 mg). LCMS (M+H$^+$): 473.

Step 5: Preparation of methyl 4-fluoro-2-[1-[(6S)-6-methyl-5-[(3,4,5-trifluorophenyl)carbamoyl]-6,7-dihydro-4H-pyrazolo[1,5-a]pyrazin-3-yl]-5-oxo-pyrrolidin-3-yl]benzoate (Compound 14f)

A mixture of (6S)-tert-butyl 3-(4-(5-fluoro-2-(methoxycarbonyl)phenyl)-2-oxopyrrolidin-1-yl)-6-methyl-6,7-dihydropyrazolo[1,5-a]pyrazine-5(4H)-carboxylate (compound 14e, 40 mg, 84.7 μmol) in DCM/TFA (1:1, 4 mL) was stirred at 20° C. for 1 hour. The reaction mixture was concentrated and the residue was dissolved in DMF (2 mL), then added N-ethyl-N-isopropylpropan-2-amine (109 mg, 847 μmol), and phenyl (3,4,5-trifluorophenyl)carbamate (intermediate I-3, 33.9 mg, 127 μmol). The reaction mixture was stirred at 70° C. for 1 hour. then the reaction mixture was diluted with EtOAc, washed with water and brine. The organic layer was concentrated to give compound 14f as light yellow oil (40 mg). LCMS (M+H$^+$): 546.

Step 6: Preparation of 4-fluoro-2-[1-[(6S)-6-methyl-5-[(3,4,5-trifluorophenyl)carbamoyl]-6,7-dihydro-4H-pyrazolo[1,5-a]pyrazin-3-yl]-5-oxo-pyrrolidin-3-yl]benzoic acid (Example 14)

A mixture of methyl 4-fluoro-2-[1-[(6S)-6-methyl-5-[(3,4,5-trifluorophenyl)carbamoyl]-6,7-dihydro-4H-pyrazolo[1,5-a]pyrazin-3-yl]-5-oxo-pyrrolidin-3-yl]benzoate (compound 14f, 30 mg, 55 μmol) and NaOH (550 μl, 1M) in MeOH (5 mL) was stirred at 20° C. for 1 hour, then the mixture was adjust to PH=6, then the solution was purified by Prep-HPLC to give Example 14 (4 mg) as white solid. LCMS (M+H$^+$): 532.2, $^1$H NMR (400 MHz, METHANOL-d$_4$) δ ppm 7.86-7.82 (m, 1H), 7.54 (s, 1H), 7.29-7.10 (m, 3H), 7.02-6.99 (m, 1H), 4.97 (dd, J=7.0, 16.9 Hz, 1H), 4.91-4.83 (m, 1H), 4.65-4.48 (m, 1H), 4.43 (dd, J=5.9, 16.9 Hz, 1H), 4.27-3.95 (m, 3H), 3.82-3.78 (m, 1H), 2.92-2.85 (m, 1H), 2.70-2.63 (m, 1H), 1.17 (d, J=6.8 Hz, 1.5H), 1.15 (d, J=6.8 Hz, 1.5H).

Example 15

5-Fluoro-2-[1-[(6S)-6-methyl-5-[(3,4,5-trifluorophenyl)carbamoyl]-6,7-dihydro-4H-pyrazolo[1,5-a]pyrazin-3-yl]-5-oxo-pyrrolidin-3-yl]benzoic acid

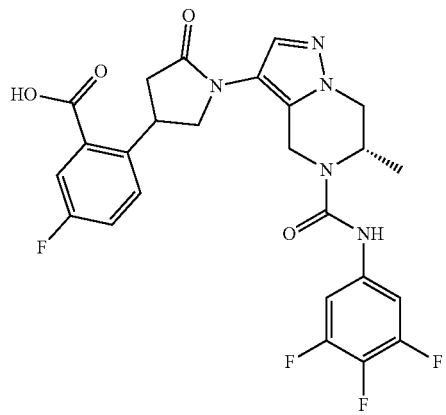 [SMILES: C[C@H]1Cn2ncc(N3CC(c4ccc(F)cc4C(=O)O)CC3=O)c2CN1C(=O)Nc1cc(F)c(F)c(F)c1]

Example 15 was prepared in analogy to Example 14 by using methyl 2-bromo-5-fluorobenzoate instead of methyl 2-bromo-4-fluorobenzoate (compound 14a). Example 15 (7 mg) was obtained as white solid. LCMS (M+H$^+$): 532.2. $^1$H NMR (400 MHz, METHANOL-d$_4$) δ ppm 7.53 (d, J=0.9 Hz, 1H), 7.51-7.41 (m, 2H), 7.26-7.09 (m, 3H), 4.96 (dd, J=7.4, 16.9 Hz, 1H), 4.89-4.81 (m, 1H), 4.54-4.37 (m, 2H), 4.23-3.99 (m, 3H), 3.82-3.74 (m, 1H), 2.91-2.85 (m, 1H), 2.68-2.64 (m, 1H), 1.17 (d, J=6.8 Hz, 1.5H), 1.15 (d, J=6.8 Hz, 1.5H).

Example 16

4-[1-[(6S)-6-methyl-5-[(3,4,5-trifluorophenyl)carbamoyl]-6,7-dihydro-4H-pyrazolo[1,5-a]pyrazin-3-yl]-5-oxo-pyrrolidin-3-yl]benzoic acid

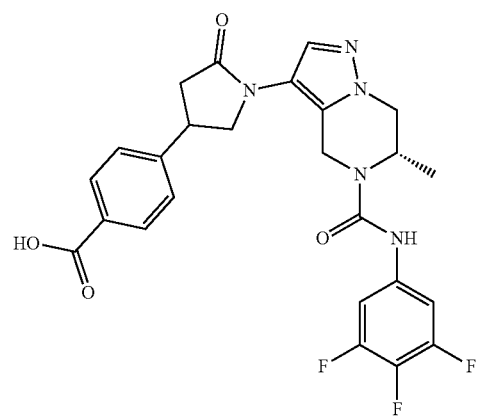 [SMILES: C[C@H]1Cn2ncc(N3CC(c4ccc(C(=O)O)cc4)CC3=O)c2CN1C(=O)Nc1cc(F)c(F)c(F)c1]

Example 16 was prepared in analogy to Example 8 by using methyl 4-iodobenzoate instead of methyl 3-iodobenzoate (compound 8a). Example 16 (120 mg) was obtained as a white solid. LCMS (M+H$^+$): 514.4, $^1$H NMR (400 MHz, METHANOL-d$_4$) δ ppm 8.07-8.03 (m, 2H), 7.68 (s, 1H), 7.55-7.50 (m, 2H), 7.33-7.25 (m, 2H), 5.14-5.03 (m, 1H), 5.01-4.91 (m, 1H), 4.61-4.49 (m, 1H), 4.34-4.15 (m, 3H), 4.00-3.91 (m, 2H), 3.06-2.97 (m, 1H), 2.84-2.75 (m, 1H), 1.29 (t, J=7.3 Hz, 3H).

Example 17

6-[1-[(6S)-6-methyl-5-[(3,4,5-trifluorophenyl)carbamoyl]-6,7-dihydro-4H-pyrazolo[1,5-a]pyrazin-3-yl]-5-oxo-pyrrolidin-3-yl]pyridine-2-carboxylic acid

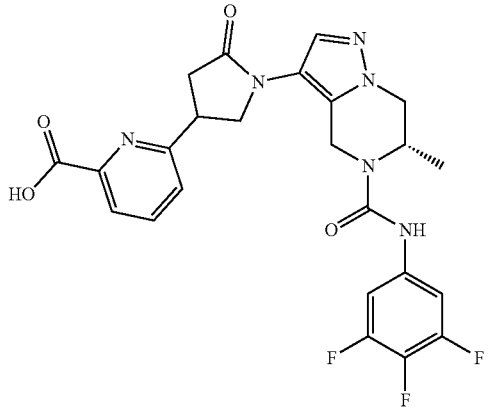 [SMILES: C[C@H]1Cn2ncc(N3CC(c4cccc(C(=O)O)n4)CC3=O)c2CN1C(=O)Nc1cc(F)c(F)c(F)c1]

Example 17 was prepared in analogy to Example 8 by using ethyl 6-bromopyridine-2-carboxylate instead of methyl 3-iodobenzoate (compound 8a). Example 17 (100 mg) was obtained as a white solid. LCMS (M+H$^+$): 515.2, $^1$H NMR (400 MHz, METHANOL-d$_4$) δ ppm 8.09 (d, J=7.2 Hz, 1H), 7.99 (t, J=7.7 Hz, 1H), 7.69 (s, 1H), 7.65 (d, J=7.4 Hz, 1H), 7.34-7.26 (m, 2H), 5.16-5.04 (m, 1H), 5.03-4.94 (m, 1H), 4.59 (t, J=16.4 Hz, 1H), 4.34-4.27 (m, 1H), 4.26-4.06 (m, 4H), 3.07-2.95 (m, 2H), 1.28 (d, J=7.0 Hz, 3H).

Example 18

2-[1-[(6S)-6-methyl-5-[(3,4,5-trifluorophenyl)carbamoyl]-6,7-dihydro-4H-pyrazolo[1,5-a]pyrazin-3-yl]-5-oxo-pyrrolidin-3-yl]pyridine-3-carboxylic acid

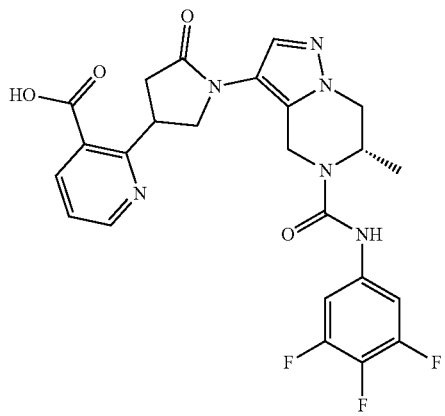 [SMILES: C[C@H]1Cn2ncc(N3CC(c4ncccc4C(=O)O)CC3=O)c2CN1C(=O)Nc1cc(F)c(F)c(F)c1]

Example 18 was prepared in analogy to Example 8 by using tert-butyl 2-bromopyridine-3-carboxylate instead of methyl 3-iodobenzoate (compound 8a). Example 18 (11 mg) was obtained as a white solid. LCMS (M+H$^+$): 515.5, $^1$H NMR (400 MHz, METHANOL-d$_4$) δ ppm 8.78-8.73 (m, 1H), 8.36-8.32 (m, 1H), 7.63 (s, 1H), 7.45-7.39 (m, 1H), 7.34-7.25 (m, 2H), 5.15-5.03 (m, 1H), 5.01-4.93 (m, 1H), 4.86-4.81 (m, 1H), 4.53 (d, J=16.9 Hz, 1H), 4.34-4.23 (m, 2H), 4.20-4.13 (m, 1H), 4.10-3.99 (m, 1H), 3.04-2.96 (m, 2H), 1.32-1.24 (m, 3H).

Example 19

HBV Inhibition Assays

Cell Line and Culture Conditions:
HepG2.2.15 is a stably-transfected cell line containing the HBV genome. It is derived from the hepatoblastoma cell line Hep G2 (American Type Culture Collection, ATCC® HB-8065™) by the published procedures described in reference: MA Selles et al. Proc. Natl. Acad. Sci. USA 1987, 84, 1005-1009. The cell line was maintained in Dulbecco's modified Eagle's medium and nutrient mixture F-12 (DMEM/F-12, Gibco, Cat.#: 11320-033) supplemented with 10% fetal bovine serum (Gibco, Cat.#:10099-141), 100 U/mL penicillin, 100 μg/mL streptomycin (Gibco, Cat.#: 15140-122), and 0.3 mg/mL of G418 Sulfate (Gibco, Cat.#: 10131-027).

ANTI-HBV activity in vitro:
HepG2.2.15 cells were seeded into 96-well plates at a density of 3×10$^4$ cells per well in culture media of 100 μL DMEM/F-12 supplemented with 2.5% fetal bovine serum, 100 U/mL penicillin, 100 μg/mL streptomycin and cultured overnight at 37° C. The test compounds were serially half-log diluted in DMSO, then diluted 100 times in culture media. 100 μL culture media containing diluted compounds were added into the plates to reach 0.5% final concentration of DMSO in every well. Five days after compound treatment, culture supernatant was collected for further analysis.

For quantitative PCR detection of extracellular HBV DNA, culture supernatant was processed by 500 μg/mL Proteinase K (Sigma, Cat.#:P2308) digestion at 50° C. for 1 hour. After heat inactivation of the enzyme at 95° C. for 15 minutes, the samples were subjected to HBV DNA quantification by qPCR. The effective compound concentration at which HBV replication was inhibited by 50% (EC$_{50}$) was determined.

The Examples of the present invention were tested in the above assays as described herein and found to have EC$_{50}$<0.5 μM in HepG2.2.15 assay as shown in Table 1 below.

TABLE 1

Activity of compounds of this invention in HepG2.2.15 assay

| Example No. | EC$_{50}$ (μM) |
| --- | --- |
| 1 | 0.126 |
| 2 | 0.098 |
| 3 | 0.139 |
| 4 | 0.105 |
| 5 | 0.240 |
| 6-1 | 0.112 |
| 6-2 | 0.099 |
| 7 | 0.022 |
| 7-1 | 0.034 |
| 7-2 | 0.014 |
| 8 | 0.089 |
| 9 | 0.124 |

TABLE 1-continued

Activity of compounds of this invention in HepG2.2.15 assay

| Example No. | EC$_{50}$ (μM) |
|---|---|
| 10-1 | 0.106 |
| 10-2 | 0.017 |
| 11-1 | 0.312 |
| 11-2 | 0.077 |
| 12 | 0.288 |
| 13 | 0.099 |
| 14 | 0.030 |
| 15 | 0.057 |
| 16 | 0.228 |
| 18 | 0.102 |

The invention claimed is:

1. A compound of formula (I)

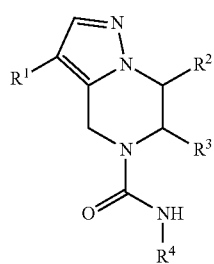

wherein:
R$^1$ is oxooxadiazabicyclo[3.3.1]nonanyl substituted by carboxyC$_{1-6}$alkyl; or oxopyrrolidinyl, said oxopyrrolidinyl being once substituted by carboxyC$_{1-6}$alkyl (C$_{1-6}$ alkyl)amino, carboxyphenyl, carboxypyridinyl, carboxyphenylamino, halocarboxyphenyl or carboxypyrrolidinyl, or twice substituted by carboxypyrrolidinyl and C$_{1-6}$alkyl;
R$^2$ is H or C$_{1-6}$alkyl;
R$^3$ is C$_{1-6}$alkyl; and
R$^4$ is phenyl, said phenyl being three times substituted by halogen;
or a pharmaceutically acceptable salt, enantiomer or diastereomer thereof.

2. A compound according to claim 1, wherein:
R$^1$ is carboxymethyl(methyl)aminooxopyrrolidinyl, carboxypyrrolidinyloxopyrrolidinyl, carboxypyrrolidinyl(methyl)oxopyrrolidinyl, carboxyphenyloxopyrrolidinyl, carboxypyridinyloxopyrrolidinyl, carboxyphenylaminooxopyrrolidinyl, fluorocarboxyphenyloxopyrrolidinyl or carboxymethyloxooxadiazabicyclo[3.3.1]nonanyl;
R$^2$ is H or methyl;
R$^3$ is methyl; and
R$^4$ is trifluorophenyl;
or a pharmaceutically acceptable salt, enantiomer or diastereomer thereof.

3. A compound selected from:
(2S)-1-[1-[(6S)-6-methyl-5-[(3,4,5-trifluorophenyl)carbamoyl]-6,7-dihydro-4H-pyrazolo[1,5-a]pyrazin-3-yl]-5-oxo-pyrrolidin-3-yl]pyrrolidine-2-carboxylic acid;
(2S)-1-[(2S)-2-methyl-1-[(6S)-6-methyl-5-[(3,4,5-trifluorophenyl)carbamoyl]-6,7-dihydro-4H-pyrazolo[1,5-a]pyrazin-3-yl]-5-oxo-pyrrolidin-3-yl]pyrrolidine-2-carboxylic acid;
2-[methyl-[1-[(6S)-6-methyl-5-[(3,4,5-trifluorophenyl)carbamoyl]-6,7-dihydro-4H-pyrazolo[1,5-a]pyrazin-3-yl]-5-oxo-pyrrolidin-3-yl]amino]acetic acid;
(2R)-1-[(2S)-2-methyl-1-[(6S)-6-methyl-5-[(3,4,5-trifluorophenyl)carbamoyl]-6,7-dihydro-4H-pyrazolo[1,5-a]pyrazin-3-yl]-5-oxo-pyrrolidin-3-yl]pyrrolidine-2-carboxylic acid;
1-[1-[(6S)-6-methyl-5-[(3,4,5-trifluorophenyl)carbamoyl]-6,7-dihydro-4H-pyrazolo[1,5-a]pyrazin-3-yl]-5-oxo-pyrrolidin-3-yl]pyrrolidine-3-carboxylic acid;
(2S)-1-[1 -[(6S,7S)-6,7-dimethyl-5-[(3,4,5-trifluorophenyl)carbamoyl]-6,7-dihydro-4H-pyrazolo[1,5-a]pyrazin-3-yl]-5-oxo-pyrrolidin-3-yl]pyrrolidine-2-carboxylic acid;
2-[1-[(6S)-6-methyl-5-[(3,4,5-trifluorophenyl)carbamoyl]-6,7-dihydro-4H-pyrazolo[1,5-a]pyrazin-3-yl]-5-oxo-pyrrolidin-3-yl]benzoic acid;
3-[1-[(6S)-6-methyl-5-[(3,4,5-trifluorophenyl)carbamoyl]-6,7-dihydro-4H-pyrazolo[1,5-a]pyrazin-3-yl]-5-oxo-pyrrolidin-3-yl]benzoic acid;
(2R)-1-[1-[(6S)-6-methyl-5-[(3,4,5-trifluorophenyl)carbamoyl]-6,7-dihydro-4H-pyrazolo[1,5-a]pyrazin-3-yl]-5-oxo-pyrrolidin-3-yl]pyrrolidine-2-carboxylic acid;
3-fluoro-2-[1-[(6S)-6-methyl-5-[(3,4,5-trifluorophenyl)carbamoyl]-6,7-dihydro-4H-pyrazolo[1,5-a]pyrazin-3-yl]-5-oxo-pyrrolidin-3-yl]benzoic acid;
2-fluoro-6-[1-[(6S)-6-methyl-5-[(3,4,5-trifluorophenyl)carbamoyl]-6,7-dihydro-4H-pyrazolo[1,5-a]pyrazin-3-yl]-5-oxo-pyrrolidin-3-yl]benzoic acid;
2-[[1-[(6S)-6-methyl-5-[(3,4,5-trifluorophenyl)carbamoyl]-6,7-dihydro-4H-pyrazolo[1,5-a]pyrazin-3-yl]-5-oxo-pyrrolidin-3-yl]amino]benzoic acid;
2-[7-[(6S)-6-methyl-5-[(3,4,5-trifluorophenyl)carbamoyl]-6,7-dihydro-4H-pyrazolo[1,5-a]pyrazin-3-yl]-6-oxo-3-oxa-7,9-diazabicyclo[3.3.1]nonan-9-yl]acetic acid;
4-fluoro-2-[1-[(6S)-6-methyl-5-[(3,4,5-trifluorophenyl)carbamoyl]-6,7-dihydro-4H-pyrazolo[1,5-a]pyrazin-3-yl]-5-oxo-pyrrolidin-3-yl]benzoic acid;
5-fluoro-2-[1-[(6S)-6-methyl-5-[(3,4,5-trifluorophenyl)carbamoyl]-6,7-dihydro-4H-pyrazolo[1,5-a]pyrazin-3-yl]-5-oxo-pyrrolidin-3-yl]benzoic acid;
4-[1-[(6S)-6-methyl-5-[(3,4,5-trifluorophenyl)carbamoyl]-6,7-dihydro-4H-pyrazolo[1,5-a]pyrazin-3-yl]-5-oxo-pyrrolidin-3-yl]benzoic acid;
6-[1-[(6S)-6-methyl-5-[(3,4,5-trifluorophenyl)carbamoyl]-6,7-dihydro-4H-pyrazolo[1,5-a]pyrazin-3-yl]-5-oxo-pyrrolidin-3-yl]pyridine-2-carboxylic acid; and
2-[1-[(6S)-6-methyl-5-[(3,4,5-trifluorophenyl)carbamoyl]-6,7-dihydro-4H-pyrazolo[1,5-a]pyrazin-3-yl]-5-oxo-pyrrolidin-3-yl]pyridine-3 -carboxylic acid, or a pharmaceutically acceptable salt thereof.

4. A process for preparing a compound according to claim 1 comprising the following step:
reacting a compound of formula (V),

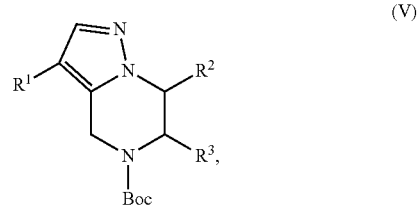

with an acid followed by urea formation with amine $R^4NH_2$ in the presence of a phosgene equivalent; wherein $R^1$, $R^2$, $R^3$ and $R^4$ are defined as in claim 1.

5. A pharmaceutical composition comprising a compound in accordance with claim 1, or a pharmaceutically acceptable salt, enantiomer or diastereomer thereof, and a therapeutically inert carrier.

6. A method for the treatment of hepatitis B virus infection, which method comprises administering to a patient in need thereof a therapeutically effective amount of a compound as defined in claim 1, or a pharmaceutically acceptable salt, enantiomer or diastereomer thereof.

* * * * *